United States Patent
Vidovic et al.

(10) Patent No.: US 11,453,637 B2
(45) Date of Patent: *Sep. 27, 2022

(54) SITE-SPECIFIC ISOTOPIC LABELING OF 1,4-DIENE SYSTEMS

(71) Applicant: Retrotope, Inc., Los Altos, CA (US)

(72) Inventors: Dragoslav Vidovic, Belgrade (RS); Mikhail Sergeevich Shchepinov, Oxford (GB)

(73) Assignee: Retrotope, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/708,124

(22) Filed: Dec. 9, 2019

(65) Prior Publication Data

US 2020/0109103 A1 Apr. 9, 2020

Related U.S. Application Data

(63) Continuation of application No. 16/192,387, filed on Nov. 15, 2018, now Pat. No. 10,577,304, which is a
(Continued)

(51) Int. Cl.
*C07B 59/00* (2006.01)
*C07C 11/12* (2006.01)
(Continued)

(52) U.S. Cl.
CPC ............ *C07C 67/30* (2013.01); *C07B 59/001* (2013.01); *C07C 5/00* (2013.01); *C07C 11/12* (2013.01);
(Continued)

(58) Field of Classification Search
CPC ....... C07C 67/30; C07C 11/12; C07C 51/347; C07B 59/001; C07B 2200/05
See application file for complete search history.

(56) References Cited

U.S. PATENT DOCUMENTS 3,520,872 A 7/1970 Wechter
4,792,620 A 12/1988 Paulik et al.
(Continued)

FOREIGN PATENT DOCUMENTS

CN 1114878 A 1/1996
EP 0713653 A1 5/1996
(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX. (Year: 2005).*
(Continued)

*Primary Examiner* — Deborah D Carr
(74) *Attorney, Agent, or Firm* — Mintz Levin/Retrotope

(57) ABSTRACT

Methods for preparing isotopically modified 1,4-diene systems from non-isotopically modified 1,4-dienes involve selective oxidation of one or more bis-allylic position(s), or the preparation of isotopically modified 1,4-diene systems via trapping pi-allylic complexes with a source of deuterium or tritium. Such methods are useful for preparing isotopically modified polyunsaturated lipid including polyunsaturated fatty acids and polyunsaturated fatty acid derivatives.

19 Claims, 4 Drawing Sheets

Related U.S. Application Data continuation of application No. 15/778,182, filed as application No. PCT/US2016/051119 on Sep. 9, 2016.

(60) Provisional application No. 62/258,993, filed on Nov. 23, 2015.

(51) Int. Cl.

| | | |
|---|---|---|
| *C07C 67/30* | (2006.01) | |
| *C07C 5/00* | (2006.01) | |
| *C07C 407/00* | (2006.01) | |
| *C07C 29/00* | (2006.01) | |
| *C07C 51/347* | (2006.01) | |
| *C07C 69/587* | (2006.01) | |
| *A61P 1/16* | (2006.01) | |

(52) U.S. Cl.
CPC ............ *C07C 29/00* (2013.01); *C07C 51/347* (2013.01); *C07C 69/587* (2013.01); *C07C 407/00* (2013.01); *A61P 1/16* (2018.01); *B01J 2531/822* (2013.01); *C07B 2200/05* (2013.01); *C07C 2523/46* (2013.01); *C07C 2531/22* (2013.01); *C07C 2531/24* (2013.01)

(56) References Cited

U.S. PATENT DOCUMENTS

| | | | |
|---|---|---|---|
| 5,130,061 | A | 7/1992 | Cornieri et al. |
| 5,194,448 | A | 3/1993 | Coupland et al. |
| 5,436,269 | A | 7/1995 | Yazawa et al. |
| 5,709,888 | A | 1/1998 | Gil et al. |
| 5,843,497 | A | 12/1998 | Sundram et al. |
| 5,914,347 | A | 6/1999 | Grinda |
| 6,111,066 | A | 8/2000 | Anderson, III et al. |
| 6,369,247 | B1 | 4/2002 | Miller et al. |
| 6,417,233 | B1 | 7/2002 | Sears et al. |
| 6,503,478 | B2 | 1/2003 | Chaiken et al. |
| 7,271,315 | B2 | 9/2007 | Metz et al. |
| 7,381,558 | B2 | 6/2008 | Barclay |
| 10,011,620 | B2 | 7/2018 | Brabet et al. |
| 10,577,304 | B2 * | 3/2020 | Vidovic ............... C07B 59/001 |
| 2001/0023259 | A1 | 9/2001 | Slabas et al. |
| 2002/0198177 | A1 | 12/2002 | Horrobin |
| 2004/0043013 | A1 | 3/2004 | McCleary |
| 2005/0147665 | A1* | 7/2005 | Horrobin ............... A61K 31/70 424/456 |
| 2005/0164908 | A1 | 7/2005 | Ginsberg et al. |
| 2006/0035382 | A1 | 2/2006 | Shinozaki et al. |
| 2006/0116535 | A1 | 6/2006 | Ito et al. |
| 2006/0205685 | A1 | 9/2006 | Phiasivongsa et al. |
| 2006/0241088 | A1 | 10/2006 | Arterburn et al. |
| 2007/0004639 | A1 | 1/2007 | Kane et al. |
| 2007/0032548 | A1 | 2/2007 | Ellis |
| 2008/0234197 | A1 | 9/2008 | Allam et al. |
| 2009/0054504 | A1 | 2/2009 | Bozik et al. |
| 2009/0069354 | A1 | 3/2009 | Czarnik |
| 2009/0182022 | A1 | 7/2009 | Rongen et al. |
| 2009/0215896 | A1 | 8/2009 | Morseman et al. |
| 2009/0232916 | A1 | 9/2009 | Shulman et al. |
| 2009/0306015 | A1 | 12/2009 | Gately et al. |
| 2009/0326070 | A1 | 12/2009 | Freeman et al. |
| 2010/0022645 | A1 | 1/2010 | Nelson et al. |
| 2010/0160248 | A1 | 6/2010 | Shchepinov |
| 2011/0028434 | A1 | 2/2011 | Destaillats et al. |
| 2011/0028493 | A1 | 2/2011 | Matsunaga et al. |
| 2011/0082206 | A1 | 4/2011 | Miller |
| 2011/0105609 | A1 | 5/2011 | Shchepinov |
| 2011/0190195 | A1 | 8/2011 | Atlas |
| 2018/0339958 | A1 | 11/2018 | Vidovic et al. |

FOREIGN PATENT DOCUMENTS

| | | |
|---|---|---|
| EP | 1548116 A1 | 6/2005 |
| EP | 1834639 A1 | 9/2007 |
| EP | 1961311 A1 | 8/2008 |
| EP | 2641891 A1 | 9/2013 |
| FR | 2721518 A3 | 12/1995 |
| JP | H01-070439 U | 5/1989 |
| JP | 2-237919 | 9/1990 |
| JP | H05246938 A | 9/1993 |
| JP | H8-268885 A | 10/1996 |
| JP | H9-143492 A | 6/1997 |
| JP | 2010-291955 | 11/1998 |
| JP | 2000-290291 A | 10/2000 |
| JP | 2001-145880 | 5/2001 |
| JP | 2001-514239 A | 9/2001 |
| JP | 2001-270832 A | 10/2001 |
| JP | 2001-519355 A | 10/2001 |
| JP | 2002-513911 A | 5/2002 |
| JP | 2002-527387 A | 8/2002 |
| JP | 2002-536981 A | 11/2002 |
| JP | 2004-81156 A | 3/2004 |
| JP | 2004-520848 A | 7/2004 |
| JP | 2004-530635 A | 10/2004 |
| JP | 2005-510501 A | 4/2005 |
| JP | 2006-502081 A | 1/2006 |
| JP | 2006-504701 A | 2/2006 |
| JP | 2006-510669 A | 3/2006 |
| JP | 2007-230876 A | 9/2007 |
| JP | 2008-504372 A | 2/2008 |
| JP | 2009-007337 A | 1/2009 |
| JP | 2009-502745 A | 1/2009 |
| JP | 2009-525948 A | 7/2009 |
| JP | 2010-521493 A | 6/2010 |
| JP | 2011502113 A | 1/2011 |
| JP | 2013509439 A | 3/2013 |
| KR | 10-2005-0029582 A | 3/2005 |
| WO | WO-99/56790 | 11/1999 |
| WO | WO-00/21524 A1 | 4/2000 |
| WO | WO-01/17374 A1 | 3/2001 |
| WO | WO-02/096221 A2 | 12/2002 |
| WO | WO-03/035095 A1 | 5/2003 |
| WO | WO-2003/051348 A2 | 6/2003 |
| WO | WO-03/064576 A2 | 8/2003 |
| WO | WO-2004/028536 | 4/2004 |
| WO | WO-2004/029254 | 4/2004 |
| WO | WO-2004/052227 | 6/2004 |
| WO | WO-2005/037848 | 4/2005 |
| WO | WO-2007/049098 | 5/2007 |
| WO | WO-2007/081910 | 7/2007 |
| WO | WO-2007/102030 | 9/2007 |
| WO | WO-2008/143642 | 11/2008 |
| WO | WO-2009/017833 | 2/2009 |
| WO | 2009056983 A1 | 5/2009 |
| WO | WO-2009/097331 | 8/2009 |
| WO | WO-2009/114809 | 9/2009 |
| WO | WO-2009/114814 | 9/2009 |
| WO | WO-2009/123316 | 10/2009 |
| WO | WO-2009/151125 | 12/2009 |
| WO | WO-2010/010365 | 1/2010 |
| WO | WO-2010/014585 | 2/2010 |
| WO | WO-201 0/068867 | 6/2010 |
| WO | WO-2010/106211 | 9/2010 |
| WO | WO-2010/132347 | 11/2010 |
| WO | WO-2010/143053 | 12/2010 |
| WO | WO-2011/053870 | 5/2011 |
| WO | WO-2011/097273 | 8/2011 |
| WO | WO-2012/148926 | 11/2012 |
| WO | WO-2012/148927 | 11/2012 |
| WO | WO-2012/148929 | 11/2012 |
| WO | WO-2012/148930 | 11/2012 |
| WO | WO-2012/174262 | 12/2012 |
| WO | 2015/138773 A2 | 9/2015 |

OTHER PUBLICATIONS

Aldrich, Handbook of Fine Chemicals and Laboratory Equipment, 2002, Milwaukee, WI, p. 811. (Year: 2002).*

(56) References Cited

OTHER PUBLICATIONS

CRC, CRC Handbook of Chemistry and Physics, 1989, CRC Press, Inc., Boca Raton, FL, pp. B-228-B-229. (Year: 1989).*
Asfari Z. et al., "Molecular modelling and chemical synthesis of molecular 'Mappemondes' designed from a Calix[4]-bis-crown", Tetra. Lett. 1996; 37(19):3325-3328.
Atzrodt, V. et al., "The renaissance of H/D exchange", Chem. Int. Ed. 2007, 46(41):7744-7765.
Barton D.H.R. et al., "Radical mono- and dideoxygenations with the triethylsilane + benzoyl peroxide system", Tetra. Lett. 1991; 32(49):7187-7190.
Brook A.G. et al., "Reaction of a silene with a silacyclopropane to yield a disilacyclopropone", Organometalics. 1985, 4(8):1487-1488.
Catino, A.J. et al., "Dirhodium(II) caprolactamate: An exceptional catalyst for allylic oxidation", J Am Chem Soc. 2004;126(42):13622-13623 and Supporting Information in 4 pages.
Choi, H. et al., "Optimal TBHP Allylic Oxidation of $\Delta^5$-Steroids Catalyzed by Dirhodium Caprolactamate", Org Lett. 2007; 9(26):5349-5352.
Corberán J., et al., Highly stable Cp*-Ir(III) complexes with N-heterocyclic carbine ligands as C-H activation catalysts for the deuteration of organic molecules, J Am Chern Soc. 2006, 128(12):3974-3979.
Cunnane S.C., "Problems with essential fatty acids: time for a new paradigm?", Prog Lipid Res. 2003; 42(6):544-568.
Di Giuseppe A. et al., "Mild and selective H/D exchange at the β position of aromatic α-olefins by N-heterocyclic carbine-hydride-rhodium catalysts", Angew Chem Int Ed Engl. 2011, 50(17):3938-3942.
Do T.Q. et al., "Enhanced sensitivity of ubiquinone-deficient mutants of Saccharomyces cerevisiae to products of autoxidized polyunsaturated fatty acids", PNAS USA 1996; 93(15):7534-7539.
Erdogan G. et al., "Mild and selective deuteration and isomerization of alkenes by a bifunctional catalyst and deuterium oxide", J Am Chem Soc. 2009, 131(30):10354-10355 and Supporting Information in 18 pages.
Erdogan G. et al., "Catalysis of Selective Hydrogen/Deuterium Exchange at Allylic Positions Using Deuterium Oxide", 2010, Topics in Catalysis. 53(15-18):1055-1058.
Faller J. W. et al., "Stereoselective vinylic carbon-hydrogen activation by a homogeneous iridium catalyst", Organometallics. 1989, 8(3):602-609.
Feng Y. et al., Effect of Ancillary Ligands and Solvents on H/D Exchange Reactions Catalyzed by Cp*lr Complexes. Organometallics. 2010, 29(13):2857-2867 with Supporting Information in 9 pages.
Firsov et al., "Threshold protective effect of deuterated polyunsaturated fatty acids on peroxidation of lipid bilayers", *The FEBS Journal* (2019), pp. 1-19.
Furrow M.E. et al., "Practical procedures for the preparation of N-tert_butyldimethylsilylhydrazones and their use in modified Wolff-Kishner reductions and in the synthesis of vinyl halides and gem-dihalides", J Am Chem Soc. 2004; 126(17):5436-5445.
Gant T.G., "Using deuterium in drug discovery: leaving the label in the drug", J Med Chem. 2014, 57(9):3595-3611.
Greene D.L. et al., "Dinitriles as Ligands. II. Derivatives of Cobalt and Nickel Perchlorates", Inorg Nucl Chem Letters, 1974, 10:895-898.
Grotjahn D.B. et al., "Extensive Isomerization of Alkenes Using a Bifunctional Catalyst:Å An Alkene Zipper", J Am Chem Soc. 2007, 129:9592-9593.
Hatano M. et al., "Selective H/D Exchange at Vinyl and Methylidene Groups with D2O Catalyzed by an Iridium Complex", Org Lett. 2016, 18(15):3674-3677 with Supporting Information in 44 pages.
Huynh H.V. et al., "Syntheses and catalytic activities of Pd(II) dicarbene and hetero-dicarbene complexes", J Organomet Chem. 2011, 696(21):3369-3375.

Jacquot et al., "Isotope Sensitive Branching and Kinetic Isotope Effects in the Reaction of Deuterated Arachidonic Acids with Human 12- and 15-Lipoxygenases", *Biochemistry*, vol. 47, No. 27, pp. 7295-7303, Jul. 1, 2008.
Khaskin E. et al., "Simple and Efficient Catalytic Reaction for the Selective Deuteration of Alcohols", ACS Catal. 2013, 3(3):448-452 with Supporting Information in 10 pages.
Koritala et al. "Deuteration of methyl linoleate with nickel, palladium and copper-chromite catalysts", J Am Oil Chem Soc. 1973, 50(8)310-316.
Krishnamurthy S. et al., "Facile Reduction of Alkyl Tosylates with Lithium Triethylborohydride. An Advantageous Procedure for Deoxygenation of Cyclic and Acyclic Alcohols", J. Org. Chem. 1976, 41(18):3064-3066.
Krishnamurthy S., "Rapid Reduction of Alkyl Tosylates with Lithium Triethylborohydride. A Convenient and Advantageous Procedure for the Deoxygenation of Simple and Hindered Alcohols. Comparison of Various Hydride Reagents", J Oranomet Chem. 1978, 156:171-181.
Kurita T. et al. "Efficient and Convenient Heterogeneous Palladium-Catalyzed Regioselective Deuteration at the Benzylic Position", Chemistry—A European Journal. 2008, 14(2):664-673 and supporting information.
Lee S.H. et al., "Catalytic H/D Exchange of Unactivated Aliphatic C-H Bonds", Organometallics 2013, 32(21):6599-6604 with Supporting Information in 55 pages.
Lowry T.R. et al.,"Definition: Carpene" in *Mechanism and Theory in Organic Chemistry* 256 (Harper & Row, 1976) Table of Contents; p. 256.
Maity R. et al., "Metal center dependent coordination modes of a tricarbene ligand", Chem Commun (Camb), 2013, 49(10):1011-1013.
Naik A et al., "Iron(II)-bis(isonitrile) complexes: novel catalysts in asymmetric transfer hydrogenations of aromatic and heteroaromatic ketones", Chem Commun.(Camb), 2010, 46(25):4475-4477.
Negre-Salvayre A. et al., "Advanced lipid peroxidation end products in oxidative damage to proteins. Potential role in diseases and therapeutic prospects for the inhibitors", Brit. J Pharmacol. 2008; 153(1):6-20.
Neubert L. et al., "Ruthenium-catalyzed selective α,β-deuteration of bioactive amines", J Am Chem Soc. 2012,134(29):12239-12244 and Supporting Information in 17 pages.
Prechtl M.H. et al., "H/D exchange at aromatic and heteroaromatic hydrocarbons using D2O as the deuterium source and ruthenium dihydrogen complexes as the catalyst", Angew Chem Int Ed Engl. 2007, 46(13):2269-2272.
Rybtchinski B. et al., "Aromatic vs aliphatic C-H bond activation by rhodium(I) as a function of agostic interactions: catalytic H/D exchange between olefins and methanol or water", J Am Chem Soc. 2003, 125(36):11041-11050 and Supporting Information in 22 pages.
Sajiki H., "Development of deuterium labeling method based on the heterogeneous platinum group metal-catalyzed C-H activation", The Pharmaceutical Society of Japan—Yakugaku Zasshi., 2013, 133(11) pp. 1177-1193, English Abstract.
Shilov A.E. et al., "Activation ofCminus signH Bonds by Metal Complexes", Chem Rev., 1997, 97(8):2879-2932.
Tao J. et al., "Mechanism of alkene isomerization by bifunctional ruthenium catalyst: A theoretical study", J Organomet Chem., 2012, 698:1-6.
Tse S.K.S. et al., "Hydrogen/Deuterium Exchange Reactions of Olefins with Deuterium Oxide Mediated by the Carbonylchlorohydrido-tris(triphenylphosphine)ruthenium(II) Complex", Adv Synth Catal. 2010, 352(9):1512-1522.
Tse S.K., "Ruthenium-catalyzed regioselective deuteration of alcohols at the β-carbon position with deuterium oxide", Chemistry, 2011, 17(49):13918-13925 and Supporting Information in 12 pages.
Vértes A.et al., [Eds], "Physiological effect of Heavy Water", in *Handbook of Nuclear Chemistry*—.Elements and isotopes: formation, transformation, distribution, vol. 2; Kluwer Acad Publ. (2003) Chapter 4; Section 9.1.; Table of Contents and pp. 110-116.
Vowinkel E. et al., "A simple Method for the Reduction of Alcohols to Hydrocarbons", Chem Ber. (1974) 107:1353-1359.

(56) References Cited

OTHER PUBLICATIONS

Watanabe Y. et al., "A radical deoxygenation of secondary alcohols to hydrocarbons by use of tributyltin hydride", Tetrahed Lett. 1986; 27(44):5385-5388.
Yu R.P. et al., "Iron-catalysed tritiation of pharmaceuticals", Nature 2016, 529(7585):195-199.
Yung C.M et al., "Stoichiometric and catalytic H/D incorporation by cationic iridium complexes: a common monohydrido-iridium intermediate", J Am Chem Soc. 2004, 126(40):13033-13043.
International Search Report and Written Opinion dated Dec. 8, 2016 for corresponding PCT/US2016/051119, filed Sep. 9, 2016.
Hammarstrom, "Stereospecific Elimination of Hydrogen at C-10 in Eicosapentaenoic Acid During the Conversion to Leukotriene C5," Journal of Biological Chemistry, 1983, vol. 258 (3), pp. 1427-1430 (5 pages).
Shoten, Iwanami, "Eicosapentaenoic Acid," Biodictionary, Apr. 10, 1997, p. 114 (2 pages).
Notice of Reasons of Rejection dated Sep. 17, 2020 received in related Japanese Patent Application No. 2018-526719 with English translation (15 pages).
Angelova, P., et al., "Lipid peroxidation is essential for a-synuclein-induced cell death," Journal of Neurochemistry, Jan. 10, 2015, pp. 582-589 (8 pages).
Andreyev, A., et al., "Isotope-reinforced polyunsaturated fatty acids protect mitochondria from oxidative stress," Free Radical Biology and Medicine, Jan. 8, 2015, 82, pp. 63-72 (10 pages).
Lamberson, C., et al., Unusual Kinetic Isotope Effects of Deuterium Reinforced Polyunsaturated Fatty Acids in Tocopherol-Mediated Free Radical Chain Oxidations, J Am Chern Soc., Jan. 8, 2014, 136(3), pp. 838-841 (9 pages).
Cotticelli, M. G., et al., "Insights into the role of oxidative stress in the pathology of Friedreich ataxia using peroxidation resistant polyunsaturated fatty acids," Redox Biology, Jul. 19, 2013, 1, pp. 398-404 (7 pages).
Hill, S., et al., "Small Amounts of Isotope-reinforced Polyunsaturated Fatty Acids Suppress Lipid Autoxidation," Free Radic Biol Med., Jun. 13, 2012, 53(4), pp. 893-906 (34 pages).
Shchepinov, M., et al., Isotopic reinforcement of essential polyunsaturated fatty acids diminishes nigrostriatal degeneration in a mouse model of Parkinson's Disease, Toxicology Letters, Aug. 10, 2011, 207, pp. 97-103 (7 pages).
Hill, S., et al., Isotope-Reinforced Polyunsaturated Fatty Acids Protect Yeast Cells from Oxidative Stress, Free Radic Biol Med., Oct. 16, 2010, 50(1), (23 pages).
Shchepinov, M., et al., "Isotope Effect, Essential Diet Components, and Prospects of Aging Retardation," Russian Journal of General Chemistry, Septembers, 2010, vol. 80, No. 7, pp. 1514-1522 (9 pages).
Shchepinov, M., et al., "Mitigating Effects of Oxidation in Aging and Diseases," ASENT Pipeline Session, Mar. 5, 2010 pp. 1-11 (11 pages).
Shchepinov, M., "Do "heavy" eaters live longer?" BioEssays, Nov. 16, 2007, 29, pp. 1247-1256 (10 pages).
Shchepinov, M., "Reactive Oxygen Species, Isotope Effect, Essential Nutrients, and Enhanced Longevity," Rejuvenation Research, Mar. 22, 2007, vol. 10, pp. 47-59 (13 pages).
Jacquot, et al., "Isotope Sensitive Branching and Kinetic Isotope Effects in the Reaction of Deuterated Arachidonic Acids with Human 12- and 15-Lipoxygenases," Biochemistry, Jul. 8, 2008 47(27), pp. 7295-7303 (24 pages).
Peng, et al., "Synthesis of Site-Specifically Labeled Arachidonic Acids as Mechanistic Probes for Prostaglandin H Synthase," Organic Letters, Jan. 14, 2004, vol. 6, No. 3, pp. 349-352 (4 pages).
Adams et al., Case Report: Expanded Access Treatment of an Infantile Neuroaxonal Dystrophy (INAD) Patient with a Novel, Stabilized Polyunsaturated Fatty Acid Drug, American Academy of Neurology conference, poster session, Apr. 2018 (1 page).
Adhikary et al., UVA-visible photo-excitation of guanine radical cations produces sugar radicals in DNA and model structures, Nucleic Acids Research, 2005, vol. 33, No. 17, pp. 5553-5564.
Asada et al.; Stereochemistry of meso-a,E Diaminopimelate Decarboxylase Reaction: The First Evidence for Pyriodoxal 5'-Phosphate Dependent Decarboxylation with Inversion of Configuration, Biochemistrv, 1981, vol. 20, No. 24, pp. 6881-6886.
Bada et al.; Isotopic Fractionation During Peptide Bond Hydrolysis, Geochimica et Cosmoschimica Acta, 1989, vol. 53, pp. 3337-3341.
Balasubramanian et al.; "DNA strand breaking by the hydroxyl radical is governed by the accessible surface areas of the hydrogen atoms of the DNA backbone," Proc. Natl. Acad. Sci. USA, Aug. 1998, vol. 95 pp. 9738-9743.
Brandl et al., "The biosynthesis of 3-(trans-2-Nitrocyclopropyl)alanine, a Constituent of the Signal Metabolite Hormaomycin," European Journal of Organic Chemistry, published online Dec. 20, 2004, vol. 2005, No. 1, pp. 123-135.
Brenna et al., "a-Linolenic acid supplementation and conversionton to n-3 long-chain polyunsaturated fatty acids in humans," Prostaglandins, Leukotrienes and Essential Fatty Acids; vol. 80; pp. 85-91; 2009.
Brenna et al., "High-Precision Continuous-Flow Isotope Ratio Mass Spectrometry; Mass Spectrometry Review," vol. 16; pp. 227-258; 1997.
Brenna, J.T., "Efficiency of conversion ofa-linolenicacid to long chain n-3 fatty acids in man," Lipid Metabolism; pp. 127-132; 2002.
Brenna, J.T., "Use of stable isotopes to study fatty acid and lipoprotein metabolism in man; Prostaglandins, Leukotrienes and Essential Fatty Acids," vol. 57 (4 & 5); pp. 467-472; 1997.
Burdzy et al., "Synthesis of stable-isotope enriched 5-methylpyrimidines and their use as probes of base reactivity in DNA," Nucleic Acids Research, 2002, vol. 30, No. 18, pp. 4068-4074.
Chen et al., "One-pot selective deuteriation of 5'-dimethoxytritylated deoxynucleotide derivatives," Bioorganic & Medicinal Chemistry Letters, Pergamon, Elsevier Schince, GB, vol. 4, No. 6, pp. 789-793, Mar. 24, 1994.
Chiriac et al., "Synthesis of [1,3,6,7-15N, 8-13C] adenine," Journal of Labelled Compounds and Radiopharmaceuticals; Apr. 1999 (published online May 4, 1999); vol. 42, issue 4, pp. 377-385.
Cho et al., "Cooperativity and anti-cooperativity between ligand binding and the dimerization of ristocetin A: asymmetry of a homodimer complex and implications for signal transduction," Chemistry & Bioloav; Mar. 1996; vol. 3, issue 3, pp. 207-215.
Clarke et al.."Isotope-reinforced polyunsaturated fatty acids protect yeast cells from oxidative stress," FASEB J. 2010; 24:849.2. (4 pages).
Crombie et al., "Synthesis of [14, 14-2H2]—linolenic acid and its use to confirm the pathway to 12-oxophytodienoic acid (12-oxoPDA) in plants: a conspectus of the epoxycarbonium ion derived family of metabolites from linoleic and linolenic acid hydroperoxides," Journal of the Chemical Society, Perkin Transactions 1, No. 3, 1991, pp. 581-587.
Dalle-Donne et al., "Protein carbonylation in human diseases," Elsevier Trends in Molecular Medicine, Apr. 2003, vol. 9, Issue 4, pp. 169-176.
De Sain-van der Velden, M.G. et al., "Increased VLDL in nephrotic patients results from a decreased catabolism while increased LDL results from increased synthesis," Kidney Int., Apr. 1998, vol. 53, No. 4, pp. 994-1001.
Demi Dov, V., "Heavy isotopes to avert ageing?" Elsevier Trends in Biotechnoloy, 2007, vol. 25, Issue 9, pp. 371-375.
Dentistry Dictionary reduced-size edition, Oct. 10, 1989, the first edition, pp. 2216-2217.
Dyall et al., "Neurological Benefits of Omega-3 Fatty Acids," Neuromolecular Medicine, vol. 10, No. 4, Jun. 10, 2008, pp. 219-235.
Elharram et al., "Deuterium-reinforced polyunsaturated fatty acids improve cognition in a mouse model of sporadic Alzheimer's disease," The FEBS Journal (2017) pp. 4083-4095.
Emken et al., "Influence of linoleic acid on desaturation and uptake of deuterium-labeled palmitic and stearic acids in humans", Biochimica Et Biophysica Acta—Lipids and Lipid Metabolism, Elsevier Science BV. Amsterdam, NL, vol. 1170, No. 2, Oct. 13, 1993 (Oct. 13, 1993), pp. 173-181.

(56) References Cited

OTHER PUBLICATIONS

Emken et al., "Effect of Dietary Docosahexaenoic Acid on Desaturation and Uptake in vivo of Isotope-Labeled Oleic, Linoleic, and Linolenic Acids by Male Subjects," Lipids; vol. 34, No. 8; pp. 785-791; 1999.
Emken et al., "Metabolism of cis-12-octadecenoic acid and trans-9, trans-12-octadecadienoic acid and their influence on lipogenic enzyme activities in mouse liver," Biochimica et Biophysica Acta; vol. 919; pp. 111-121; 1987.
Esaki et al., "Synthesis of base-selectively deuterium-labelled nucleosides by the Pd/C Catalyzed H-D Exchange Reaction in Deuterium Oxide," Heterocycles; 2005; vol. 66, pp. 361-369.
Evans et al., "ENDOR, triple resonance and ESR studies of spin-trapped radicals in autoxidized linoleic acid and its deuterated derivatives," Biochimica et Biophysica Acta—Lipids and Lipid Metabolism, Elsevier Science BV, Amsterdam, NL, vol. 835, No. 3, Jul. 31, 1985, pp. 421-425.
Extended European search report for European Patent Application No. 12776313 dated Sep. 17, 2014 (10 pages).
Extended European search report for European Patent Application No. 12776521 dated Sep. 17, 2014 (9 pages).
Extended European Search Report for European Patent Application No. 12777440 dated Sep. 17, 2014 by European Patent Office (11 pages).
Extended European Search Report and Written Opinion dated Jun. 5, 2013 for EP Patent Application No. 10827578.5 (13 pages).
Extended European Search Report for European Patent Application No. 12776294 dated Sep. 25, 2014 by European Patent Office.
Finglas et al., "Use of an oral/intravenous dual-label stable-isotope protocol to determine folic acid bioavailability from fortified cereal grain foods in women," The Journal of Nutrition, vol. 132, No. 5, pp. 936-939, May 2002.
Foldesi et al., "The Synthesis of Deuterionucleosides," Nucleosides, Nucleotides and Nucleic Acids; 2000, vol. 19, No. 10-12, pp. 1615-1656.
Mantena, et al., "Mitochondrial Dysfunction and Oxidative Stress in the Pathogenesis of Alcohol-and Obesity-Induced Fatty Liver Diseases," Free Radical Biology & Medicine, Oct. 16, 2008, vol. 44, pp. 1259-1272.
Geboes et al., "Validation of a new test meal for a protein digestion breath test in humans," The Journal of Nutrition, vol. 134, No. 4, pp. 806-810, Apr. 2004.
Giordano, F. J., "Oxygen, oxidative stress, hypoxia, and heart failure," The Journal of Clinical Investigation, Mar. 2005, vol. 115, No. 3, pp. 500-508.
Gueraud et al., "Chemistry and biochemistry of lipid peroxidation products," Free Radical Research, Oct. 2010, vol. 44, No. 10, pp. 1098-1124.
Harman, Denham, "Aging and Oxidative Stress," Journal of International Federation of Clinical Chemistry (JIFCC), vol. 10, No. 1; pp. 24-26; Mar. 1998.
Harman, Denham, "The Free Radical Theory of Aging; Antioxidants & Redox Signaling," vol. 5, No. 5, pp. 557-561, Oct. 2003.
Cicalese, L. et al., Hepatocellular. Hepatocellular carcinoma. Medscape Reference. 2014;1-5.
Hill et al., "Isotope-reinforced polyunsaturated fatty acids protect yeast cells from oxidative stress," Free Radical Biology & Medicine, Jan. 1, 2011, vol. 50 (23 pages).
Hill et al., "Small amounts of isotope-reinforced polyunsaturated fatty acids suppress lipid autoxidation," Free Radical Biology and Medicine, vol. 53, 2012 (34 pages).
Hulme et al., "Chemistry and the Worm: Caenorhabditis elegans as a Platform for Integrating Chemical and Biological Research," Chemical Biology; Angewandte Chemie International Edition; vol. 50; pp. 4774-4807, 2011.
Hussein, N.,"Long-chain conversion of [13C] linoleic acid and -linolenic acid in response to marked changes in their dietary intake in men," The Journal of Lipid Research, vol. 46, No. 2, Dec. 1, 2004, pp. 269-280.

Ikeya et al., "Evaluation of stereo-array isotope labeling (SAIL) patterns for automated structural analysis of proteins with CYANA," Magnetic Resonance in Chemistry, Jul. 2006, vol. 44, spec. No. S152-S157.
Schutt, "Proteins Modified by Malondialdehyde, 4-Hydroxynoneneal, or Advanced Glycation End Products in Lipofuscin of Human Retinal Pigment Epithelium," IOVS, Aug. 2003, vol. 44, No. 8, pp. 3663-3668.
Jacquot et al., "Isotope Sensitive Branching and Kinetic Isotope Effects in the Reaction of Deuterated Arachidonic Acids with Human 12- and 15-Lipoxygenases," Biochemistry, vol. 47, No. 27, pp. 7295-7303, Jul. 8, 2008 (24 pages).
Junk T. et al., "Hydrogen isotope exchange reactions involving C-H (D, T) bonds", Chem Soc Rev. 1997, 26:401-406.
Japanese Journal of Clinical Medicine (Separate Volume) Syndrome classified as New Fields Series 13 Liver/Biliary Tract-based Syndrome (second edition) I Liver edition (the first volume) Sep. 20, 2010 pp. 196-201.
Johnson et al., "Potential role of dietary n-3 fatty acids in the prevention of dementia and macular degeneration," The American Journal of Clinical Nutrition, vol. 83, No. 6, Jun. 2006, pp. 1494S-1498S and 1555 (6 pages).
Yasuji, et al., "Primary Sclerosing Cholangitis and Carcinogenesis," Journal of Biliary Tract & Pancreas, 2005, vol. 26, No. 4, pp. 351-357.
Angulo, et al., "Quadrennial Review, Non-Alcoholic Fatty Liver Disease," Journal of Gastroenterology and Hepatology, 2002, vol. 17, Suppl., pp. S186-S190.
Yoneya, et al., "Genetic polymorphisms as risk factors for coronary artery disease," Japanese Journal of Clinical Medicine, Oct. 1, 1998 , vol. 56, No. 10, pp. 51-56 (2509-2514).
Kelland et al., "Stereochemistry of Lysine Formation by meso-Diaminopimelate Decarboxylase from Wheat Germ: Use of 1H-13C NMR Shift Correlation to Detect Stereospecific Deuterium Labeling," Biochemistry, Jun. 1985, vol. 24, No. 13, pp. 3263-2367.
Kelly, S et al. "Assessing the authenticity of single seed vegetable oils using fatty acid stable carbon isotope ratios (13C/12C)," Food Chemistry. 1997, vol. 59, No. 2. Elsevier Science Ltd. , pp. 181-186.
King et al., "Mitochondria-derived Reactive Oxygen Species Mediate Blue Light-induced Death of Retinal Pigment Epithelial Cells," Photochemistry and Photobiology, 2004, 79(5): 470-475 (Year: 2004).
Kishore et al., "Partial 13C Isotopic Enrichment of Nucleoside Monophosphates: Useful Reporters for NMR Structural Studies," Nucleic Acids Research; Oct. 2005, vol. 33, No. 18, e164, pp. 1-10.
Knapp et al., "Temperature-dependent isotope effects in soybean lipoxygenase-1: Correlating hydrogen tunneling with protein dynamics," JAGS Articles; J. Am. Chem. Soc.; vol. 124; pp. 3865-3874; published online Mar. 20, 2002.
Kushner et al., "Pharmacological uses and perspectives of heavy water and deuterated compounds," Canadian Journal of Physiology and Pharmacology; Feb. 1999; vol. 77, pp. 79-88.
Lambert D., "Rationale and applications of lipids as prodrug carriers," European Journal of Pharmaceutical Sciences. 2000;11 (Suppl.2): S 15-S27.
Lefkowitz et al., "Where Does the Developing Brain Obtain Its Docosahexaenoic Acid? Relative Contributions of Dietary a-Linolenic Acid, Docosahexaenoic Acid, and Body Stores in the Developing Rat," Pediatric Research; vol. 57, No. I; pp. 157-165, 2005.
Lei et al., "Dietary omega-3 Polyunsaturated Fatty Acids Enhance Adiponectin Expression and Protect Against Pressure Overload-Induced Left Ventricular Hypertrophy and Dysfunction," Journal of Cardial Failure, Churchill Livingstone, Naperville, Il, US, vol. 13m No. 6, Aug. 1, 2007, p. S79.
Levenson et al., "The Healing of Rat Skin Wounds," Annals of Surgery, vol. 161, No. 2; pp. 293-308; Feb. 1965.
Lichtenstein, AH et al., "Comparison of deuterated leucine, valine and lysine in the measurement of human apolipoprotein AI and B-100 kinetics," Journal of Lipid Research, vol. 31, No. 9, 1990 pp. 1693-1702.
Lin et al., "Whole body distribution of deuterated linoleic and a-linolenic acids and their metabolites in the rat," Journal of Lipid Research, 2007, vol. 48; pp. 2709-2724.

(56) References Cited

OTHER PUBLICATIONS

Machteld van Lieshout et al., "Isotopic tracer techniques for studying the bioavailability and bioefficacy of dietary carotenoids, particularly β-carotene, in humans: a review," Am J Clin Nutr., Jan. 2003, vol. 77, No. 1, 12-28.
Mattison, L. K. et al., "Rapid identification of dihydropyrimidine dehydrogenase deficiency by using a novel 2-13C-uracil breath test," Clin. Cancer Res., Apr. 15, 2004, vol. 10, No. 8, pp. 2652-2658.
Mazza et al., "Omega-3 fatty acids and antioxidants in neurological and psychiatric diseases: An overview, Progress in Neuro-Psychopharmacology & Biological Psychiatry," Oxford, GB, vol. 31, No. 1, Dec. 22, 2006, pp. 12-26.
Mitsumoto et al., "Oxidative Stress Biomarkers in Sporadic ALS," Amyotroph Lateral Seier. (2008); 9(3): 177-183 (13 pages).
Nass et al., "Caenorhabditis elegans in Parkinson's Disease Drug Discovery: Addressing an Unmet Medical Need; Molecular Interventions," vol. 8, Issue 6; pp. 284-293; Dec. 2008.
Nelson et al., "Reduction of beta-Amyloid Levels by Novel Protein Kinase C epsilon Activators," Journal of Biological Chemistry, vol. 284, No. 50, Dec. 2009, pp. 34514-34521.
Liuzzi, et al., "Inhibitory Effect of Polyunsaturated Fatty Acids on MMP-9 Release from Microglial Cells—Implications for Complementary Multiple Sclerosis Treatment," Neurochem. Res., 2007, vol. 32, pp. 2184-2193.
Nobuo Tamiya and Takehiko Shimanouchi, "Infra-red absorption spectra of deuterated aspartic acids," Spectrochimica Acta, vol. 18, No. 7, pp. 895-905; Jul. 1, 1962.
Norskov et al., Nature Chemistry, Towards the computational Design of Solid Catalysts, 2009, 1, pp. 37-46. (Year: 2009).
Notice of Reasons for Rejection dated Aug. 24, 2011 for Japanese Patent Application No. 2008-557833 (12 pages).
Oba et al., "A simple route to L-[5,5,6,6-D4] lysine starting from L-pyroglutamic acid," Japanese Journal of Deuterium Science, 2006, vol. 12, No. 1, pp. 1-5.
Office Action for Japanese Patent Application No. 2014-508486 dated Dec. 25, 2015 (14 pages).
Office Action for Japanese Patent Application No. 2014-508487 dated Dec. 3, 2015 (17 pages).
Office Action for Japanese Patent Application No. 2014-508488 dated Dec. 4, 2015 (15 pages).
Office Action for Japanese Patent Application No. 2014-508489 dated Dec. 25, 2015 (15 pages).
Office Action for U.S. Appl. No. 14/551,450 dated Apr. 15, 2015 by U.S. Patent and Trademark Office (12 pages).
Ovide-Bordeaux et al., "Docosahexaenoic acid affects insulin deficiency- and insulin resistance-induced alterations in cardiac mitochondria," Am J Physiol Regul Interg Comp Physiol 286: R519-R527, 2004.
Pedersen et al., "Protein Modification by the Lipid Peroxidation Product 4-Hydroxynoneal in the Spinal Cords of Amyotrophic Lateral Sclerosis Patients," Annals of Neurology (Nov. 1998), vol. 44, Issue 5, pp. 819-824.
Raap et al., "Enantioseletive syntheses of isotopically labeled a-amino acids. Preparation of (E-13C)-L- a-aminoadipic acid and five isotopomers of L-lysine with 13C, 15N, and 2H in the o- and E-positions;," RecueildeTravauxChimiaues de Pavs-Bas, 1990, vol. 109, No. 4, pp. 277-286.
Rapoport et al., "Delivery and turnover of plasma-derived essential PUFAs in mammalian brain," Journal of Lipid Research; May 2001; vol. 42; pp. 678-685.
Zesiewicz et al., "Randomized, Clinical Trial of RTOO1: Early Signals of Efficacy in Friedreich1 s Ataxia," Published online Apr. 6, 2018 in Wiley Online Library (wileyonlinelibrary.com). DOI: 10.1002/mds.27353 (10 pages).
Reddy P. H., "Mitochondrial Medicine for Aging and Neurodegenerative Diseases," Neuromolecular Med. (2008) 10(4): 291-315 (39 pages).
Ren et al, "Simultaneous metabolic labeling of cells with multiple amino acids: localization and dynamics of histone acetylation and methylation," Proteomics: Clinical Applications; Jan. 2007; vol. 1, No. 1, pp. 130-142.
Riediger et al., "A Systemic Review of the Roles of n-3 Fatty Acids in Health and Disease," Journal of the American Dietetic Association, Apr. 2009, pp. 668-679.
Rohwedder et al., "Measurement of the Metabolic Interconversion of Deuterium-Labeled Fatty Acids by Gas Chromatography/Mass Spectrometry," Lipids; vol. 25, No. 7; pp. 401-405; 1990.
Rosell et al., "Total Syntheses of Two bis-Allylic-Deuterated DHA Analogues", Asian J. Org. Chem. 2017, 6, 322-334.
Rosen et al., "Effect of Deuterium Oxide on Wound Healing, Collagen and Metabolism of Rats," New England Journal of Medicine; vol. 270, No. 22; pp. 1142-1149; May 28, 1964.
Rustin et al., "Effect of idebenone on cardiomyopathy in Friedreich's ataxia: a preliminary study," The Lancet, 354:477-479, 1999.
Barber et al., "Oxidative Stress in ALS: A Mechanism of Neurodegeneration and a Therapeutic Target," Biochimica et Biophysica Acta 1762 (2006) 1051-1067.
Salem et al., "Arachidonic and docosahexaenoic acids are biosynthesized from their 18-carbon precursors in human infants," Proc. Natl. Acad. Sci.; vol. 93; pp. 49-54; Jan. 1996.
Scholl et al. "Synthesis of 5,5,6,6-D4-L-lystine-aflatoxin B1 for use as a mass spectrometric internal standard," Journal of Labelled Compounds & Radiopharmaceuticals; Oct. 2004; vol. 47, No. 11, pp. 807-815.
Separate Volume/Advances in Medical Science Oxidative Stress Ver.2 Oct. 5, 2006, pp. 23 to 27.
Serhiyenko Vet al., "Simvastatin and Omega-Polyunsaturated Fatty Acids in the Treatment of Cardiomyopathy in Type 2 Diabetes Mellitus Patients," Atherosclerosis Supplements, Elsevier, Amsterdam, NL, vol. 9, No. 1, May 1, 2008, p. 203.
Shah et al., "Resolving the Role of Lipoxygenases in the Initiation and Execution of Ferroptosis," ACS Cent. Sci., 2018, 4 (3), pp. 387-396; online publication Feb. 7, 2018.
Shchepinov et al., "Isotopic reinforcement of essential polyunsaturated fatty acids diminishes 8 nigrostriatal degeneration in a mouse model of Parkinson's disease," Toxicology Letter, Elsevier Biomedical Press, Amsterdam, NL, vol. 207, No. 2, pp. 97-103, Aug. 10, 2011.
Shchepinov et al., "Isotope effect, essential diet components, and prospects of aging retardation," Russian Journal of General Chemistry, 2010, vol. 80, No. 7, pp. 1514-1522.
Shchepinov et al., "Mitigating effects of oxidation in aging and diseases," Retrotope, 2010; 1-11.
Shchepinov, Mikhail, "Reactive Oxygen Species, Isotope Effect, Essential Nutrients, and Enhanced Longevity," Rejuvenation Research; 2007; vol. 10, No. 1, pp. 47-59.
Simpson et al., "Increased Lipid Peroxidation in Sera of ALS Patients," Neurology. May 25, 2004;62(10):1758-65.
Smarun et al., "Site-Specific Deuteration of Polyunsaturated Alkenes," J. Org. Chem. 2017, 82, 13115-13120.
Sumbalova et al., "Brain energy metabolism in experimental chronic diabetes: effect of long-term administration of coenzyme Q10 and w-3 polyunsaturated fatty acids," Biologia Bratislava, 60(17):105-108, 2005.
Svedruzic et al., The Mechanism of Target Base Attack in DNA Cytosine Carbon 5 Methylation; Biochemistry; Aug. 2004; vol. 43, No. 36, pp. 11460-11473.
Tang et al., "Kinetic and biochemical analysis of the mechanism of action of lysine 5, 6-aminomutase," Archives of Biochemistry and Biophysics; Oct. 2003; vol. 418, No. 1, pp. 49-54.
Aldrich, Handbook of Fine Chemicals and Laboratory Equipment, Milwaukee, WI, p. 811. (Year: 2002).
Duncan, et al., "A Nonsense Mutation in COQ9 Causes Autosomal-Recessive Neonatal-Onset Primary Coenzyme $Q_{10}$ Deficiency: A Potentially Treatable Form of Mitochondrial Disease," The American Journal of Human Genetics, May 15, 2009, vol. 84, pp. 558-566.
Taber DF et al., "Preparation of Deuterated Arachidonic Acid," Prostaglandins, Sep. 1981 vol. 22 NO. 3, 349-352.

(56) References Cited

OTHER PUBLICATIONS

Townend et al., "Dietary Macronutrient Intake and Five-year Incident Cataract: The Blue Mountains Eye Study," American Journal of Ophthalmology, Elsevier, Amsterdam, NL, vol. 143, No. 6, May 22, 2007, pp. 932-939.
Toyama et al., "Assignments and hydrogen bond sensitivities of UV resonance Raman bands of the C8-deuterated guanine ring," Journal of Raman Spectroscopy; Sep. 2002; vol. 33, issue 9, pp. 699-708.
Triglycerides. Medium chain triglycerides. Alternative Medicine Review. 2002; 7(5): 418-420.
Tucker et al., "The Synthesis of 11,11-Dideuterolinoleic Acid," Journal of Labelled Compounds, vol. VII, No. 1, 1970, pp. 11-15.
Veldink et al., "Intake of Polyunsaturated Fatty Acids and Vitamin E Reduces the Risk of Developing Amyotrophic Lateral Sclerosis," J Neuro Neurosurg Psychiatry. (2007) 78:367-371.
Iyengar, "Nuclear and isotopic techniques for addressing nutritional problems, with special reference to current applications in developing countries," Food and Nutrition Bulletin, vol. 23, No. 1, Mar. 2002 pp. 3-10.
Viswanathan and Cushley, "Deuterium Nuclear Magnetic Resonance Study of the Interaction of Substrates and Inhibitors with Soybean Lipoxygenase," The Journal of Biological Chemistry, vol. 256, No. 14, pp. 7155-7160, Issue of Jul. 1981.
Wade, David, "Deuterium isotope effects on noncovalent interactions between molecules," Chemic—Biological Interactions; 1999; vol. 117, No. 3, pp. 191-217.
Wendt et al., Mass spectrometry of perdeuterated molecules of biological origin fatty acid esters from Scenedesmus obliquus. Biochemistry. 1970;9 (25): 4854-4866.
Wheeler et al., "The synthesis of the 2H, 3H, and 14C-isotopomers of 2'-deoxy-2', 2'-diflourocytidine hydrochloride, an anti-tumor compound," Journal of labelled compounds and radiopharmaceuticals, John Wiley, Chichester, GB, vol. 29, No. 5, pp. 583-589, May 1, 1991.
Wilczynska-Kwiateka et al., "Asthma, allergy, mood disorders, and nutrition," European Journal of Medical research, Biomed Central Ltd. London, UK, vol. 14, No. Suppl 4, Dec. 7, 2009, pp. 248-254.
Written Opinion dated Sep. 8, 2008 for PCT/GB2007/050112 (7 pages).
Yamauchi et al., "Observation of the Pathway from Lysine to Isoprenoidal Lipid of Halophilic Archaea, Halobacterium halobium and Natrinema pallidum, Using Regiospecifically Deuterated Lysine," Bull. Chem. Soc. Jpn., vol. 74, pp. 2199-2205 (2001).
Yashodhara et al., "Omega-3 Fatty Acids: A Comprehensive Review of Their Role in Health and Disease," Postgrad Med J (2009) 85: 84-90.
Steines et al. (2000) "Stereoselective Catalytic Hydrogenation of Sorbic Acid and Sorbic Alcohol With New Cp*ru Complexes†", Chemical Communications, (3):217-218.

* cited by examiner

SITE-SPECIFIC ISOTOPIC LABELING OF 1,4-DIENE SYSTEMS

INCORPORATION BY REFERENCE TO ANY PRIORITY APPLICATIONS

This application is a continuation of U.S. application Ser. No. 16/192,387, filed Nov. 15, 2018, now U.S. Pat. No. 10,577,304, which is a continuation of U.S. application Ser. No. 15/778,182, filed May 22, 2018, now U.S. Pat. No. 10,730,821, which is the national phase under 35 U.S.C. § 371 of prior PCT International Application No. PCT/US2016/051119 having International filing date of Sep. 9, 2016, which designates the United States of America, and which claims the benefit of U.S. Provisional Application No. 62/258,993, filed Nov. 23, 2015. Each of the aforementioned applications is incorporated by reference herein in its entirety.

BACKGROUND

Field

Isotopically modified polyunsaturated lipids, mixture of isotopically modified polyunsaturated lipids, methods of making such compounds or mixture, pharmaceutical compositions and medicaments comprising such compounds or mixtures, and method of using such compounds or mixtures to treat, prevent, alleviate, or diagnose disease, disorders, or conditions are provided. Isotopically modified 1,4-diene systems such as polyunsaturated fatty acids ("PUFAs") are also disclosed.

Description of the Related Art

Oxidative damage is implicated in a wide variety of diseases including, but not limited to, mitochondrial diseases, neurodegenerative diseases, neurodegenerative muscle diseases, retinal diseases, energy processing disorders, kidney diseases, hepatic diseases, lipidemias, cardiac diseases, inflammation, and genetic disorders.

While the number of diseases associated with oxidative stress are numerous and diverse, it is well established that oxidative stress is caused by disturbances to the normal redox state within cells. An imbalance between routine production and detoxification of reactive oxygen species ("ROS") such as peroxides and free radicals can result in oxidative damage to cellular structures and machinery. Under normal conditions, a potentially important source of ROSs in aerobic organisms is the leakage of activated oxygen from mitochondria during normal oxidative respiration. Additionally, it is known that macrophages and enzymatic reactions also contribute to the generation of ROSs within cells. Because cells and their internal organelles are lipid membrane-enveloped, ROSs can readily contact membrane constituents and cause lipid oxidation. Ultimately, such oxidative damage can be relayed to other biomolecules within the membrane and the cell, such as proteins and DNA, through direct and indirect contact with activated oxygen, oxidized membrane constituents, or other oxidized cellular components. Thus, one can readily envision how oxidative damage may propagate throughout a cell give the mobility of internal constituents and the interconnectedness of cellular pathways.

Lipid-forming fatty acids are well-known as one of the major components of living cells. As such, they participate in numerous metabolic pathways, and play an important role in a variety of pathologies. Polyunsaturated Fatty Acids ("PUFAs") are an important sub-class of fatty acids. An essential nutrient is a food component that directly, or via conversion, serves an essential biological function and which is not produced endogenously or in large enough amounts to cover the requirements. For homeothermic animals, the two rigorously essential PUFAs are linoleic (cis,cis-9,12-Octadecadienoic acid; (9Z,12Z)-9,12-Octadecadienoic acid; "LA"; 18:2; n-6) and alpha-linolenic (cis,cis,cis-9,12,15-Octadecatrienoic acid; (9Z,12Z,15Z)-9,12,15-Octadecatrienoic acid; "ALA"; 18:3; n-3) acids, formerly known as vitamin F (Cunnane S C. Progress in Lipid Research 2003; 42:544-568). LA, by further enzymatic desaturation and elongation, is converted into higher n-6 PUFAs such as arachidonic (AA; 20:4; n-6) acid; whereas ALA gives rise to a higher n-3 series, including, but not limited to, eicosapentaenoic acid (EPA; 20:5; n-3) and docosahexaenoic (DHA; 22:6; n-3) acid (Goyens P L. et al. Am. J. Clin. Nutr. 2006; 84:44-53). Because of the essential nature of certain PUFAs or PUFA precursors, there are many known instances of their deficiency and these are often linked to medical conditions. Furthermore, many PUFA supplements are available over-the-counter, with proven efficiency against certain ailments (See, for example, U.S. Pat. Nos. 7,271,315 and 7,381,558).

PUFAs endow mitochondrial membranes with appropriate fluidity necessary for optimal oxidative phosphorylation performance. PUFAs also play an important role in initiation and propagation of the oxidative stress. PUFAs react with ROS through a chain reaction that amplifies an original event (Sun M, Salomon R G, J. Am. Chem. Soc. 2004; 126:5699-5708). However, non-enzymatic formation of high levels of lipid hydroperoxides is known to result in several detrimental changes. Indeed, Coenzyme Q10 has been linked to increased PUFA toxicity via PUFA peroxidation and the toxicity of the resulting products (Do T Q et al, PNAS USA 1996; 93:7534-7539). Such oxidized products negatively affect the fluidity and permeability of their membranes; they lead to oxidation of membrane proteins; and they can be converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20).

A logical way to obviate the damage associated with ROS would be to neutralize them with antioxidants. However, the success of antioxidant therapies has so far been limited. This may be due to several reasons, including (1) the near-saturating amount of antioxidants already present in living cells and the stochastic nature of the ROS inflicted damage, (2) the importance of ROS in cell signaling and hormetic (adaptive) upregulation of protective mechanisms, (3) the pro-oxidant nature of some antioxidants such as vitamin E, (4) the non-radical nature of PUFA peroxidation products, which can no longer be quenched with most antioxidants.

SUMMARY

Some embodiments provide for a method of preparing isotopically modified 1,4-diene systems comprising oxidizing a 1,4-diene at the bis-allylic position to afford a peroxide; and inserting an isotope at the oxidized bis-allylic position. In some embodiments, oxidizing a bis-allylic position of a 1,4-diene utilizes a transition metal selected from Rhodium, Iridium, Nickel, Platinum, Palladium, Aluminum, Titanium, Zirconium, Hafnium, or Ruthenium. In other embodiments, the transition metal is a rhodium(II) metal or a ruthenium(III) metal. In some embodiments, inserting an isotope at the oxidized bis-allylic position further comprises reducing a peroxide at the bis-allylic position to afford an alcohol. In other embodiments, amalgamated aluminum or a phosphine reduces a peroxide. In some embodiments, inserting an isotope at an oxidized bis-allylic position further comprises exchanging an alcohol with an isotope. In other embodiments, tributyltin deuteride exchanges an alcohol with deuterium.

Some embodiments provide for a method of preparing isotopically modified 1,4-diene systems comprising oxidizing an alcohol at a bis-allylic position to afford a ketone; and reducing the ketone to afford an isotopically substituted methylene group at the bis-allylic position. In other embodiments, reducing a ketone utilizes Wolff-Kishner reaction conditions.

Some embodiments provide for a method of preparing isotopically modified 1,4-diene systems comprising forming one or more pi-allylic complexes between a 1,4-diene and a metal; and inserting one or more isotopes in one or more bis-allylic positions. In some embodiments, the metal is selected from Ni, Pd and Ir. In other embodiments, the one or more pi-allylic complexes are formed as six-membered rings. In some embodiments, two or more pi-allylic complexes are formed as six-membered rings. In other embodiments, the isotope is one or more deuterium atoms.

In some embodiments, any one or more of the chemical transformations can be repeated to introduce one or more isotopes at one or more bis-allylic positions.

In some embodiments, the 1,4-diene system is a PUFA. In other embodiments, the PUFA is a compound of Formula 1A, 1B, or 1C, wherein $R^5$ is a $C_a$-$C_b$ alkyl group wherein "a" and "b" of the $C_a$-$C_b$ is any one or more of 1, 2, 3, 4, or 5.

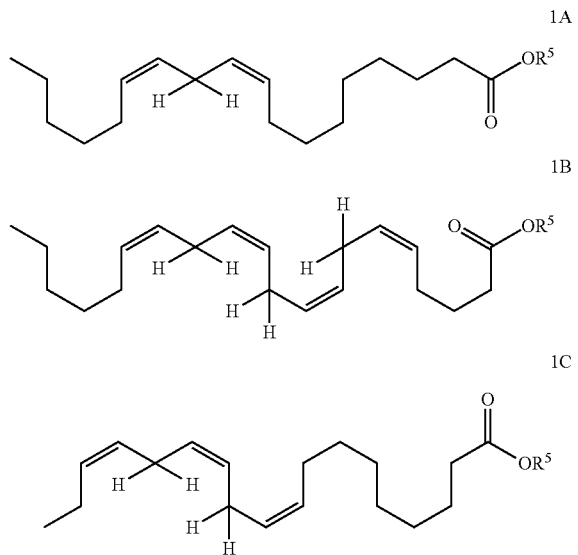

In some embodiments, the PUFA is a compound of Formula 1A and $R^5$ is a $C_1$-$C_4$ alkyl group.

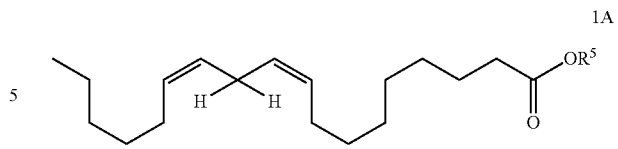

Some embodiments relate to a method for site-specifically modifying a polyunsaturated lipid with an isotope, the method comprising reacting a polyunsaturated lipid with an isotope-containing agent in a presence of a transition metal-based catalyst, whereby an isotopically-modified polyunsaturated lipid having the isotope at one or more mono-allylic or bis-allylic sites is obtained, wherein the isotope-containing agent comprises at least one isotope selected from the group consisting of deuterium, tritium, and combinations thereof.

Some embodiments relate to a method for site-specifically modifying a polyunsaturated lipid mixture with an isotope, the method comprising reacting the polyunsaturated lipid mixture with an isotope-containing agent in a presence of a transition metal-based catalyst, whereby an isotopically-modified polyunsaturated lipid mixture having the isotope at one or more mono-allylic or bis-allylic sites is obtained, wherein the isotope-containing agent comprises at least one isotope selected from the group consisting of deuterium, tritium, and combinations thereof.

Some embodiments relate to a composition comprising one or more isotopically-modified polyunsaturated lipids having an isotope predominantly at one or more allylic sites, wherein the isotope is selected from the group consisting of deuterium, tritium, and combinations thereof.

DETAILED DESCRIPTION OF THE PREFERRED EMBODIMENT

Figure 1:
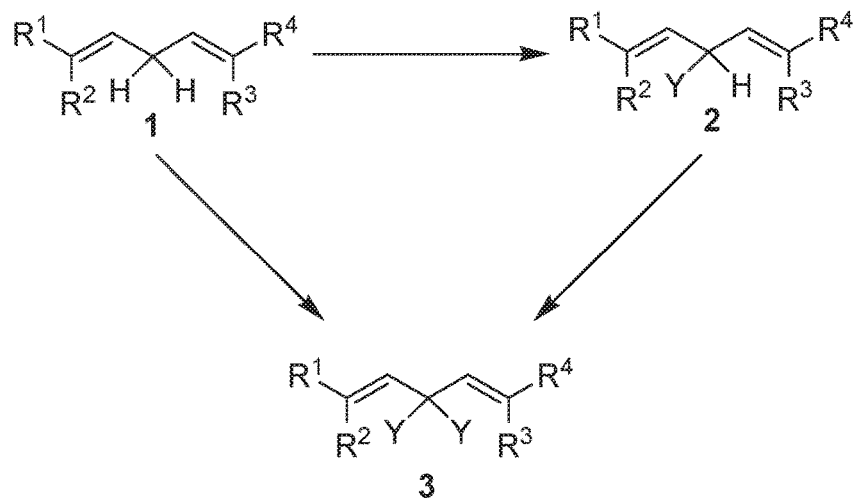
FIG. 1 is a representation of a direct exchange method for isotopically modifying 1,4-diene systems FIG. 2. is a schematic representation of methods to prepare isotopically modified 1,4-diene systems.

The section headings used herein are for organizational purposes only and are not to be construed as limiting the subject matter described.

As used herein, abbreviations are defined as follows:
ALA Alpha-linolenic acid
LIN Linoleate
LNN Linolenate
ARA Arachidonate
cap caprolactamate
D⁻ Negatively charged deuterium ion
T⁻ Negatively charged tritium ion
DHA Docosahexaenoic acid
DNA Deoxyribonucleic acid
EPA Eicosapentaenoic acid
HPLC High performance liquid chromatography
IR Infrared LA Linoleic acid
LC/MS Liquid Chromatography/Mass Spectrometry
mg milligram
mmol millimole
NMR Nuclear magnetic resonance
PUFAs Polyunsaturated fatty acids
$R_f$ Retention factor
ROS Reactive oxygen species
TBHP tert-butylhydroperoxide
TLC Thin layer chromatography
UV Ultraviolet
Cp Cyclopentadienyl As used herein, any "R" group(s) such as, without limitation, $R^1$, $R^2$, $R^3$, $R^4$, $R^5$, and $R^1$ represent substituents that can be attached to the indicated atom. An R group may be substituted or unsubstituted.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group that contains in the straight or branched hydrocarbon chain one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. An alkenyl group may be unsubstituted or substituted.

As used herein, "alkynyl" refers to an alkyl group that contains in the straight or branched hydrocarbon chain one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl. A cycloalkyl group may be unsubstituted or substituted.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "carbocyclyl" refers to all carbon ring systems. Such systems can be unsaturated, can include some unsaturation, or can contain some aromatic portion, or be all aromatic. A carbocyclyl group may be unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to ring systems including at least one heteroatom (e.g., O, N, S). Such systems can be unsaturated, can include some unsaturation, or can contain some aromatic portion, or be all aromatic. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclylic group connected, as a substituent, via a lower alkylene group. The lower alkylene and heterocyclic or a heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

The amine ligands described herein can be monodentate or multidentate and include monoamine, diamine, and triamine moieties. Monoamines can have the formula of $N(R_b)_2$, and exemplary monoamines include but are not limited to dialkylmonoamines (such as di-ra-butylamine, or DBA) and trialkylmonoamines (such as N,N-dimethylbutylamine, or DMBA). Suitable dialkylmonoamines include dimethylamine, di-ra-propylamine, di-ra-butylamine, di-sec-butyl amine, di-tert-butylamine, dipentylamine, dihexylamine, dioctylamine, didecylamine, dibenzylamine, methylethylamine, methylbutylamine, dicyclohexylamine, N-phenylethanolamine, N-(p-methyl) phenylethanolamine, N-(2,6-dimethyl) phenylethanolamine, N-(p-chloro)phenylethanolamine, N-ethylaniline, N-butyl aniline, N-methyl-2-methylaniline, N-methyl-2,6-dimethylaniline, diphenylamine, and the like, and combinations thereof. Suitable trialkylmonoamines include trimethylamine, triethylamine, tripropylamine, tributylamine, butyldimethylamine, phenyldiethylamine, and the like, and combinations thereof. Diamines can have the formula $(R^b)_2N$—$R^a$—$N(R^b)_2$, and exemplary diamines can include alkylenediamines, such as N,N'-di-ieri-butylethylenediamine, or DBEDA. Triamine refers to an organic molecule having three amine moieties, including but not limited to diethylene triamine (DETA), guanidine HCl, tetramethyl guanidine, and the like. For both the monoamine and diamine formula, $R^a$ is a substituted or unsubstituted divalent residue; and each $R^b$ is independently hydrogen, $C_1$-$C_8$ alkyl, or $C_{6-10}$ aryl. In some examples, of the above formula, two or three aliphatic carbon atoms form the closest link between the two diamine nitrogen atoms. Specific alkylenediamine ligands include those in which $R^a$ is dimethylene (—$CH_2CH_2$—) or trimethylene (—$CH_2CH_2CH_2$—). $R^b$ can be independently hydrogen, methyl, propyl, isopropyl, butyl, or a $C_4$-$C_8$ alpha-tertiary alkyl group. In some embodiments, the diamine can be ethylenediamine. In some embodiments, the triamine can be diethylenetriamine.

The alkylenediamine ligands can be monodentate or multidentate and examples include N,N,N',N' tetramethylethylene diamine (TMED), N,N'-di-tert-butylethylenediamine (DBEDA), N,N,N',N'-tetramethyl-1,3-diaminopropane (TMPD), N-methyl-1,3-diaminopropane, N,N'-dimethyl-1, 3-diaminopropane, N,N,N'-dimethyl-1,3-diaminopropane, N-ethyl-1,3-diaminopropane, N-methyl-1,4-diaminobutane, N,N'-trimethyl-1,4-diaminobutane, N,N,N'-trimethyl-1,4-diaminobutane, N,N,N',N'-tetramethyl-1,4-diaminobutane, N,N,N',N'-tetramethyl-1,5-diaminopentane, and combinations thereof. In some embodiments, the amine ligand is selected from di-ra-butylamine (DBA), N,N-dimethylbutylamine (DMBA), N,N'-di-tert-butylethylenediamine (DBEDA), and combinations thereof.

The alkene ligands described herein be monodentate or multidentate and include a molecule that has at least one non-aromatic carbon-carbon double bond and can include but are not limited to monoalkene and dialkene. Examples of the alkene ligand can include ethylene, propylene, butene, hexene, decene, butadiene, and the like.

The isonitrile ligands described herein refer to a molecule having at least one —NC moiety and can be monodentate or multidentate and include but are not limited to monoisonitrile and diisonitrile ligands. Examples of monoisonitrile and diisonitrile include but are not limited to $C_{1-10}$ alkyl-NC and CN—R—NC and R is a $C_{1-10}$ alkylene, t-butyl-NC, methyl-NC, PhP(O)(OCH$_2$CH(t-Bu)NC)$_2$, PhP(O)(OCH$_2$CH(Bn)NC)$_2$, PhP(O)(OCH$_2$CH(i-Pr)NC)$_2$, PhP(O)(OCHCH$_3$CH(i-Pr)NC)$_2$, PhP(O)(OCH$_2$CH(CH$_3$)NC)$_2$. Additional isonitrile ligands can be found in Naik et al., *Chem. Commun.*, 2010, 46, 4475-4477, which is incorporated herein by reference in its entirety.

The nitrile ligands described herein refer to a molecule having at least one —CN moiety and can be monodentate or multidentate and include but are not limited to monoisonitrile and diisonitrile ligands. Examples of monoisonitrile and diisonitrile include but are not limited to $C_{1-10}$ alkyl-CN and CN—R—CN and R is a $C_{1-10}$ alkylene, acetonitrile, 1,3,5-cyclohexanetricarbonitrile, propionitrile, butyronitrile, glutaronitrile, pivalonitrile, capronitrile, (CH$_2$)$_3$CN, (CH$_2$)$_4$CN, (CH$_2$)$_5$CN. Additional nitrile ligands can be found in Lee et al., *Inorganic and Nuclear Chemistry letters*, v10, 10 (October 1974) p. 895-898, which is incorporated herein by reference in its entirety.

The ether ligands described herein refer to a molecule having at least one R—O—R moiety wherein each R is independently an alkyl or aryl radical and can be monodentate or multidentate and include monoether, diether, and triether ligands. Examples of the monoether, diether, triether, and other suitable ether include but are not limited to dimethyl ether, diethyl ether, tetrahydrofuran, dioxane, dimethoxyethane, diethylene glycol dimethyl ether, polyethylene glycol, and anisole.

The thioether ligands described herein refer to a molecule having at least one R—S—R moiety a wherein each R is independently an alkyl or aryl radical and can be monodentate or multidentate and include monothioether, dithioether, and trithioether ligands. Examples of the monothioether, dithioether, and trithioether include but are not limited to dimethylsulfide and methyl phenyl sulfide.

The imine ligands described herein refer to a molecule having at least one carbon nitrogen double bond moiety and can be monodentate or multidentate and include monoimine, diimine, and triimine ligands. Examples of imine ligand include but are not limited to 1,2-ethanediimine, imidazolin-2-imine, 1,2-diketimine, dimethylglyoxime, o-phenylenediamine, 1,3-diketimines, and glyoxal-bis(mesitylimine).

The carbene ligands as described herein refers to compounds having at least one divalent carbon atom with only six electrons in its valence shell when not coordinated to a metal. This definition is not limited to metal-carbene complexes synthesized from carbenes, but is rather intended to address the orbital structure and electron distribution associated with the carbon atom that is bound to the metal. The definition recognizes that the "carbene" may not technically be divalent when bound to the metal, but it would be divalent if it were detached from the metal. Although many such compounds are synthesized by first synthesizing a carbene and then binding it to a metal, the definition is intended to encompass compounds synthesized by other methods that have a similar orbital structure and electron configuration. Lowry & Richardson, *Mechanism and Theory in Organic Chemistry* 256 (Harper & Row, 1976) defines "carbene" in a way that is consistent with the way the term is used herein. The carbene ligands described herein can be monocarbene, dicarbene, and tricarbene. Examples of carbene ligands include but are not limited to 1,10-dimethyl-3,30-methylenediimidazolin-2,20-diylidene, 1,10-dimethyl-3,30-ethylenediimidazolin-2,20-diylidene, 1,10-dimethyl-3,30-propylenediimidazolin-2,20-diylidene, 1,10-dimethyl-3,30-methylenedibenzimidazolin-2,20-diylidene, 1,10-dimethyl-3,30-ethylenedibenzimidazolin-2,20-diylidene, 1,10-dimethyl-3,30-propylenedibenzimidazolin-2,20-diylidene,

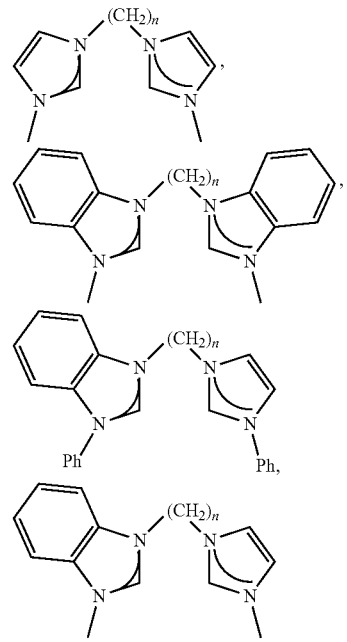

and n is 1, 2, or 3, and

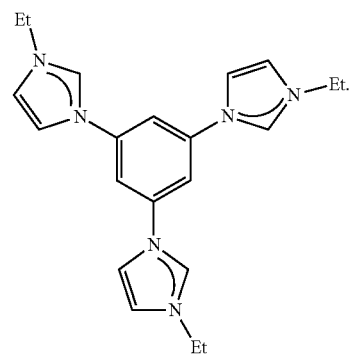 [SMILES: CCN1C=CN(c2cc(N3C=CN(CC)C3)cc(N3C=CN(CC)C3)c2)C1]

Additional carbene ligands can be found in Huynh et al., Journal of Organometallic Chemistry, v696, 21, (October 2011), p. 3369-3375, and Maity et al., *Chem. Commun.*, 2013, 49, 1011-101, which are incorporated herein by reference in their entireties.

The pyridine ligands as described herein refer to a molecule having at least one pyridine ring moiety and can include monopyridine, dipyridine, and tripyridine ligands.

Examples of the pyridine ligand include but are not limited to 2,2'-bypiridine, and 2,6-Di(2-pyridyl) pyridine.

The phosphine ligands as described herein refer to a molecule having at least one $P(R^4)_3$, and each $R^4$ is independently selected from the group consisting of hydrogen, optionally substituted $C_{1-15}$ alkyl, optionally substituted $C_{3-8}$ cycloalkyl, optionally substituted $C_{6-15}$ aryl, and optionally substituted 4-10 membered heteroaryl. The phosphine ligand can include monophosphine, bisphosphine, and trisphosphine. Examples of suitable phosphine ligand can include but are not limited to PH3, trimethylphosphine, triphenylphosphine, methyldiphenylphosphine, trifluorophosphine, trimethylphosphite, triphenylphosphite, tricyclohexylphosphine, dimethylphosphinomethane (dmpm), dimethylphosphinoethane (dmpe), PROPHOS, PAMP, DIPAMP, DIOP, DuPHOS, $P(tBu)_2Ph$, 1,2-Bis(diphenylphosphino)ethane (dppe), 1,1'-Bis(diphenylphosphino) ferrocene (dppf), 4-(tert-butyl)-2-(diisopropylphosphaneyl)-1H-imidazole, $P(t-Bu)_2(C_6H_5)$.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

The term "polyunsaturated lipid," as used herein, refers to a lipid that contains one or more unsaturated bonds, such as a double or a triple bond, in its hydrophobic tail. The polyunsaturated lipid here can be a polyunsaturated fatty acid, polyunsaturated fatty acid ester, polyunsaturated fatty acid thioester, polyunsaturated fatty acid amide, polyunsaturated fatty acid mimetic, or polyunsaturated fatty acid prodrug.

The term "mono-allylic site", as used herein, refers to the position of the polyunsaturated lipid, such as polyunsaturated fatty acid or ester thereof, that corresponds to a methylene group attached to only one vinyl group and is not adjacent to two or more vinyl group. For example, the mono-allylic site in a (9Z,12Z)-9,12-Octadecadienoic acid (linoleic acid) include the methylene groups at carbon 8 and carbon 14 positions.

The term "bis-allylic site," as used herein, refers to the position of the polyunsaturated lipid, such as polyunsaturated fatty acid or ester thereof, that corresponds to the methylene groups of 1,4-diene systems. Examples of polyunsaturated lipid having deuterium at one or more bis-allylic positions include but are not limited to 11,11-dideutero-cis, cis-9,12-Octadecadienoic acid (11,11-dideutero-(9Z,12Z)-9, 12-octadecadienoic acid; D2-LA); and 11,11,14,14-tetradeutero-cis,cis,cis-9,12,15-octadecatrienoic acid (11,11,14, 14-tetradeutero-(9Z,12Z,15Z)-9,12,15-octadecatrienoic acid; D4-ALA).

The term "pro-bis-allylic position," as used herein, refers to the methylene group that becomes the bis-allylic position upon desaturation. Some sites which are not bis-allylic in the precursor PUFAs will become bis-allylic upon biochemical transformation. The pro-bis-allylic positions, in addition to deuteration, can be further reinforced by carbon-13, each at levels of isotope abundance above the naturally-occurring abundance level. For example, the pro-bis-allylic positions, in addition to existing bis-allylic positions, can be reinforced by isotope substitution as shown below in Formula (2), wherein $R^1$ is alkyl, cation, or H; m=1-10; n=1-5; and p=1-10. In Formula (2), the position of the X atom represents the pro-bis-allylic position, while the position of the Y atom represents the bis-allylic position, and one or more of $X^1$, $X^2$, $Y^1$, or $Y^2$ atoms can be deuterium atoms.

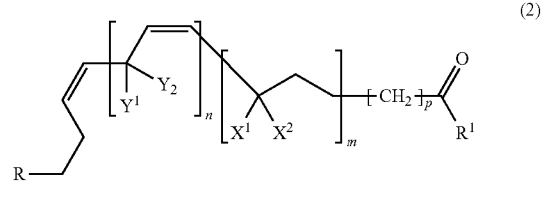

(2)

$R = H, C_3H_7; R^1 = H$, alkyl, or cation;
$Y^1$ and $Y^2$ = H or D; $X^1$ and $X^2$ = H or D Another example of a compound having bis-allylic and pro-bis-allylic positions is shown in Formula (3), wherein any of the pairs of $Y^1$-$Y^m$ and/or $X^1$-$X^m$ represent the bis-allylic and pro-bis-allylic positions of PUFAs respectively and these positions may contain deuterium atoms.

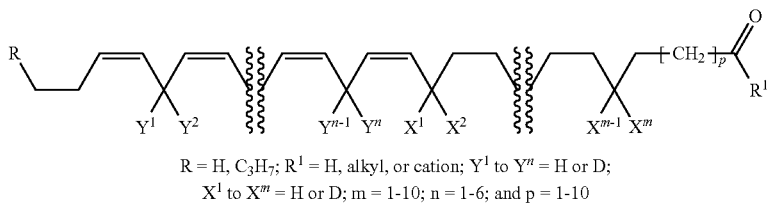

R = H, C₃H₇; R¹ = H, alkyl, or cation; Y¹ to Yⁿ = H or D;
X¹ to Xᵐ = H or D; m = 1-10; n = 1-6; and p = 1-10

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

As used herein, the term "thioester" refers to a structure in which a carboxylic acid and a thiol group are linked by an ester linkage or where a carbonyl carbon forms a covalent bond with a sulfur atom —COSR, wherein R may include hydrogen, $C_{1-30}$ alkyl (branched or straight) and optionally substituted $C_{6-10}$ aryl, heteroaryl, cyclic, or heterocyclic structure. "Polyunsaturated fatty acid thioester" refers to a structure P-COSR, wherein P is a polyunsaturated fatty acid described herein.

As used herein, the term "amide" refers to compounds or moieties that contain a nitrogen atom bound to the carbon of a carbonyl or a thiocarbonyl group such as compounds containing —C(O)NR¹R² or —S(O)N NR¹R², and R¹ and R² can independently be $C_{1-30}$ alkyl (branched or straight), optionally substituted $C_{6-10}$ aryl, heteroaryl, cyclic, heterocyclic, or $C_{1-20}$ hydroalkyl. "Polyunsaturated fatty acid amide" refers to a structure wherein the amide group is attached to the polyunsaturated fatty acid described herein through the carbon of the carbonyl moiety.

As used herein the term "prodrug" refers to a precursor compound that will undergo metabolic activation in vivo to produce the active drug. It is well-known that carboxylic acids may be converted to esters and various other functional groups to enhance pharmacokinetics such as absorption, distribution, metabolism, and excretion. Esters are a well-known pro-drug form of carboxylic acids formed by the condensation of an alcohol (or its chemical equivalent) with a carboxylic acid (or its chemical equivalent). In some embodiments, alcohols (or their chemical equivalent) for incorporation into pro-drugs of PUFAs include pharmaceutically acceptable alcohols or chemicals that upon metabolism yield pharmaceutically acceptable alcohols. Such alcohols include, but are not limited to, propylene glycol, ethanol, isopropanol, 2-(2-ethoxyethoxy)ethanol (Transcutol®, Gattefosse, Westwood, N.J. 07675), benzyl alcohol, glycerol, polyethylene glycol 200, polyethylene glycol 300, or polyethylene glycol 400; polyoxyethylene castor oil derivatives (for example, polyoxyethyleneglyceroltriricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.)); saturated polyglycolized glycerides (for example, Gelucire® 35/10, Gelucire® 44/14, Gelucire® 46/07, Gelucire® 50/13 or Gelucire® 53/10, available from Gattefosse, Westwood, N.J. 07675); polyoxyethylene alkyl ethers (for example, cetomacrogol 1000); polyoxyethylene stearates (for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, or PEG-150 distearate); ethyl oleate, isopropyl palmitate, isopropyl myristate; dimethyl isosorbide; N-methylpyrrolidinone; paraffin; cholesterol; lecithin; suppository bases; pharmaceutically acceptable waxes (for example, carnauba wax, yellow wax, white wax, microcrystalline wax, or emulsifying wax); pharmaceutically acceptable silicon fluids; sorbitan fatty acid esters (including sorbitan laurate, sorbitan oleate, sorbitan palmitate, or sorbitan stearate); pharmaceutically acceptable saturated fats or pharmaceutically acceptable saturated oils (for example, hydrogenated castor oil (glyceryl-tris-12-hydroxystearate), cetyl esters wax (a mixture of primarily C14-C18 saturated esters of C14-C18 saturated fatty acids having a melting range of about 43°-47° C.), or glyceryl monostearate).

In some embodiments, the fatty acid pro-drug is represented by the ester P-B, wherein the radical P is a PUFA and the radical B is a biologically acceptable molecule. Thus, cleavage of the ester P-B affords a PUFA and a biologically acceptable molecule. Such cleavage may be induced by acids, bases, oxidizing agents, and/or reducing agents. Examples of biologically acceptable molecules include, but are not limited to, nutritional materials, peptides, amino acids, proteins, carbohydrates (including monosaccharides, disaccharides, polysaccharides, glycosaminoglycans, and oligosaccharides), nucleotides, nucleosides, lipids (including mono-, di- and tri-substituted glycerols, glycerophospholipids, sphingolipids, and steroids). In some embodiments, alcohols (or their chemical equivalent) for incorporation into pro-drugs of PUFAs include polyalcohols such as diols, triols, tetra-ols, penta-ols, etc. Examples of alcohol include methyl, ethyl, iso-propyl, and other alkyl alcohol. Examples of polyalcohols include ethylene glycol, propylene glycol, 1,3-butylene glycol, polyethylene glycol, methylpropanediol, ethoxydiglycol, hexylene glycol, dipropylene glycol glycerol, and carbohydrates. Esters formed from polyalcohols and PUFAs may be mono-esters, di-esters, tri-esters, etc. In some embodiments, multiply esterified polyalcohols are esterified with the same PUFAs. In other embodiments, multiply esterified polyalcohols are esterified with different PUFAs. In some embodiments, the different PUFAs are stabilized in the same manner. In other embodiments, the different PUFAs are stabilized in different manners (such as deuterium substitution in one PUFA and ¹³C substitution in another PUFA). In some embodiments, the one or more PUFAs is an omega-3 fatty acid and the one or more PUFAs is an omega-6 fatty acid. In some embodiments, the ester is an ethyl ester. In some embodiments, the ester is a mono-, di- or triglyceride.

It is also contemplated that it may be useful to formulate PUFAs and/or PUFA mimetics and/or PUFA pro-drugs as salts for use in the embodiments. For example, the use of salt formation as a means of tailoring the properties of pharmaceutical compounds is well known. See Stahl et al., Handbook of pharmaceutical salts: Properties, selection and use (2002) Weinheim/Zurich: Wiley-VCH/VHCA; Gould, Salt selection for basic drugs, Int. J. Pharm. (1986), 33:201-217. Salt formation can be used to increase or decrease solubility, to improve stability or toxicity, and to reduce hygroscopicity of a drug product.

Formulation of PUFAs and/or PUFA esters and/or PUFA mimetics and/or PUFA pro-drugs as salts can include any PUFA salt described herein.

The term "polyunsaturated fatty acid mimetic," as used herein, refers to compounds that are structurally similar to naturally occurring polyunsaturated fatty acid but are non-isotopically modified to prevent hydrogen abstraction at the bis-allylic position. Various methods can be used to non-isotopically modify the polyunsaturated fatty acid to produce the polyunsaturated fatty acid mimetic, and examples include but are not limited to moving unsaturated bonds to eliminate one or more bis-allylic positions, replacing at least one carbon atom at the bis-allylic position with an oxygen or sulfur, replacing at least one hydrogen atom at the bis-allylic position with an alkyl group, replacing the hydrogen atoms at the bis-allylic position with a cycloalkyl group, and replacing at least one double bond with a cycloalkyl group.

In some embodiments, the non-isotopic modification is achieved by moving unsaturated bonds to eliminate one or more bis-allylic positions. The polyunsaturated fatty acid can have the structure of Formula (I):

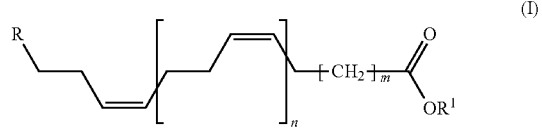

(I)

wherein R is H or $C_{1-10}$ alkyl, $R^1$ is H or $C_{1-10}$ alkyl, n is 1 to 4, and m is 1 to 12. In some embodiments, $R^1$ can be —$C_3H_7$. Examples of the polyunsaturated fatty acid mimetic include but are not limited to:

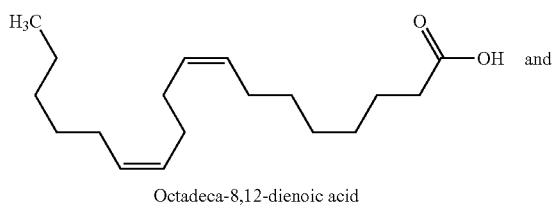

Octadeca-8,12-dienoic acid

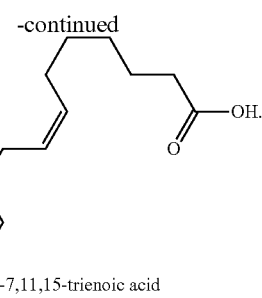

Octadeca-7,11,15-trienoic acid

In some embodiments, the non-isotopic modification is achieved by replacing at least one carbon atom at the bis-allylic position with an oxygen or sulfur. The polyunsaturated fatty acid can have the structure of Formula (II):

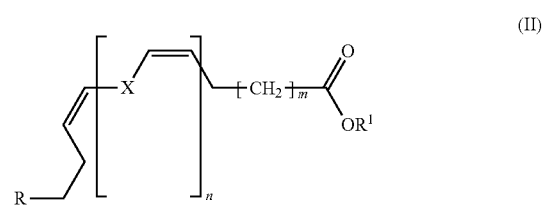

(II)

wherein R is H or $C_{1-10}$ alkyl, $R^1$ is H or $C_{1-10}$ alkyl, X is O or S, n is 1 to 4, and m is 1 to 12. In some embodiments, $R^1$ can be —$C_3H_7$. Examples of the polyunsaturated fatty acid mimetic include but are not limited to:

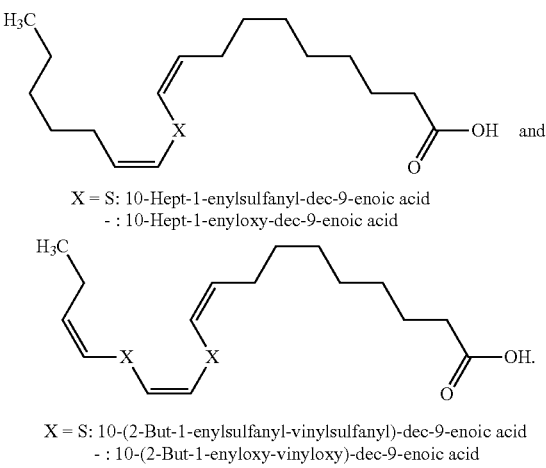

X = S: 10-Hept-1-enylsulfanyl-dec-9-enoic acid
- : 10-Hept-1-enyloxy-dec-9-enoic acid X = S: 10-(2-But-1-enylsulfanyl-vinylsulfanyl)-dec-9-enoic acid
- : 10-(2-But-1-enyloxy-vinyloxy)-dec-9-enoic acid In some embodiments, the non-isotopic modification is achieved by replacing at least one hydrogen atom at the bis-allylic position with an alkyl group. The polyunsaturated fatty acid can have the structure of Formula (III)

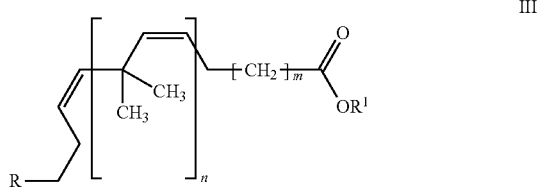

III wherein R is H or $C_{1-10}$ alkyl, $R^1$ is H or $C_{1-10}$ alkyl, X is O or S, n is 1 to 4, and m is 1 to 12. In some embodiments, $R^1$ can be —$C_3H_7$. Examples of the polyunsaturated fatty acid mimetic include but are not limited to:

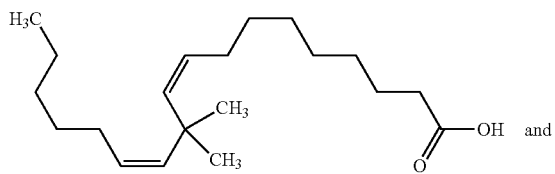

11,11-Dimethyl-octadeca-9,12-dienoic acid

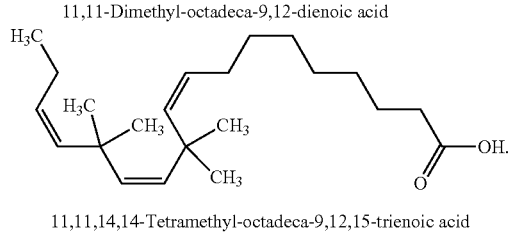

11,11,14,14-Tetramethyl-octadeca-9,12,15-trienoic acid

In some embodiments, the non-isotopic modification is achieved by replacing the hydrogen atoms at the bis-allylic position with a cycloalkyl group. The polyunsaturated fatty acid can have the structure of Formula (IV):

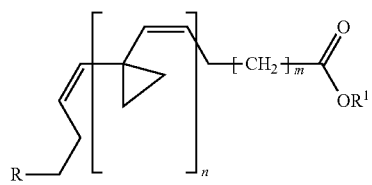

(IV)

wherein R is H or $C_{1-10}$ alkyl, $R^1$ is H or $C_{1-10}$ alkyl, n is 1 to 5, and m is 1 to 12. In some embodiments, $R^1$ can be —$C_3H_7$. Examples of the polyunsaturated fatty acid mimetic include but are not limited to:

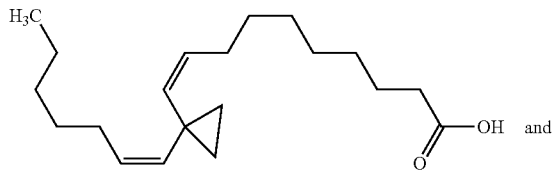

10-(1-Hept-1-enyl-cyclopropyl)-dec-9-enoic acid

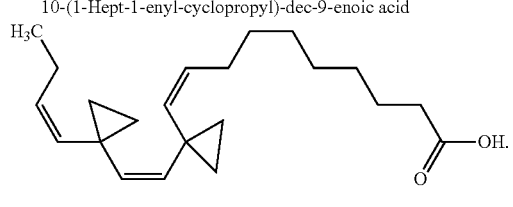

10-{1-[2-(1-But-1-enyl-cyclopropyl)-vinyl]-cyclopropyl}-dec-9-enoic acid

In some embodiments, the non-isotopic modification is achieved by replacing at least one double bond with a cycloalkyl group. The polyunsaturated fatty acid can have the structure of Formula (V), (VI), or (VII)

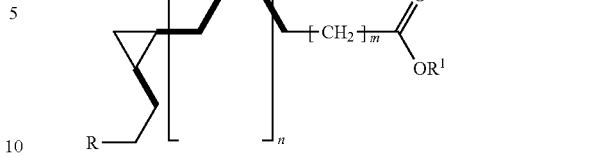

(V)

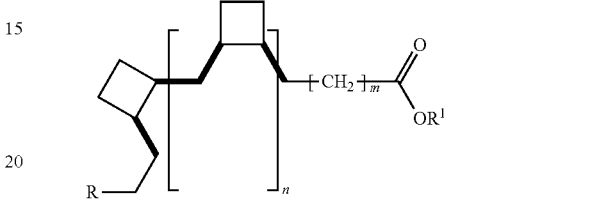

(VI)

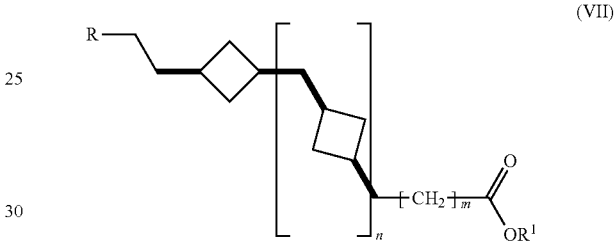

(VII)

wherein R is H or $C_{1-10}$ alkyl, $R^1$ is H or $C_{1-10}$ alkyl, n is 1 to 5, and m is 1 to 12. In some embodiments, $R^1$ can be —$C_3H_7$. Examples of the polyunsaturated fatty acid mimetic include but are not limited to:

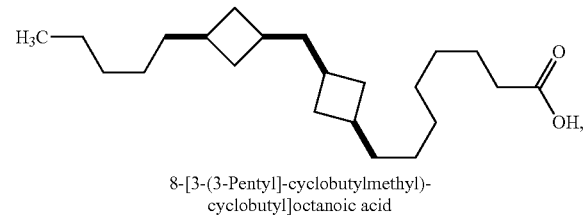

8-[3-(3-Pentyl)-cyclobutylmethyl)-cyclobutyl]octanoic acid

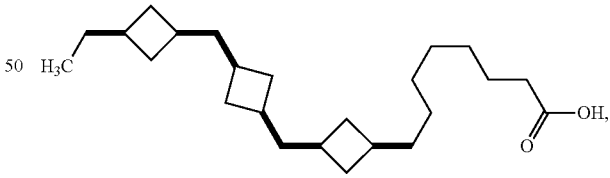

8-{3-[3-(3-Ethyl-cyclobutylmethyl)-cyclobutylmethyl]-cyclobutyl}-octanoic acid

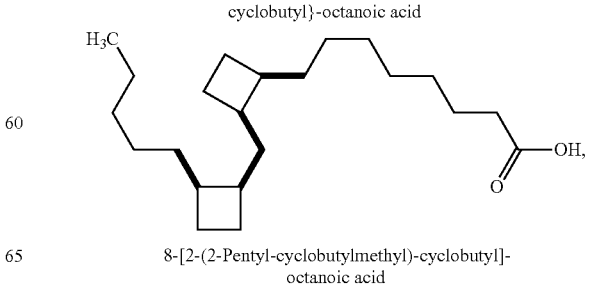

8-[2-(2-Pentyl-cyclobutylmethyl)-cyclobutyl]-octanoic acid

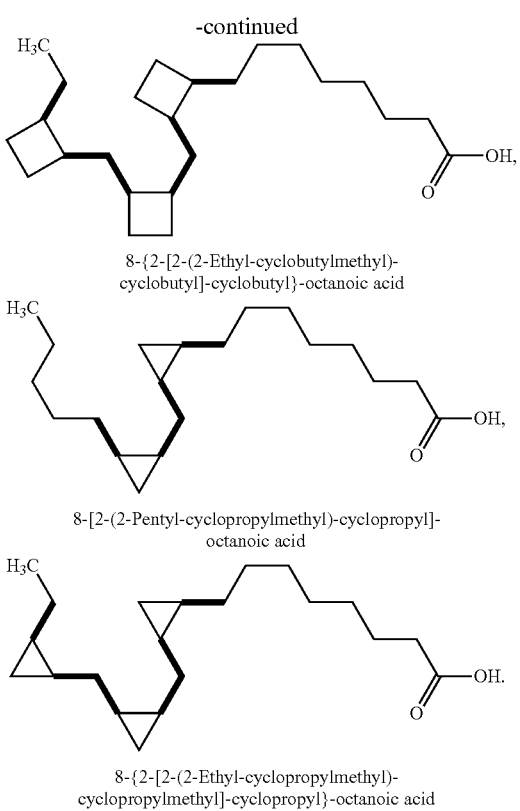

8-{2-[2-(2-Ethyl-cyclobutylmethyl)-cyclobutyl]-cyclobutyl}-octanoic acid

8-[2-(2-Pentyl-cyclopropylmethyl)-cyclopropyl]-octanoic acid

8-{2-[2-(2-Ethyl-cyclopropylmethyl)-cyclopropylmethyl]-cyclopropyl}-octanoic acid As used herein, "predominantly" refers to about 40% or greater. In one embodiment, predominantly refers to greater than about 40%, 45%, 50%, 55%, 60%, 65%, 70%, 75%, 80%, 85%, 90%, 95% or 100%. In one embodiment, predominantly refers to about 40%, 45%, 50%, 55%, 60%, 65%, 70%, 75%, 80%, 85%, 90%, 95% or 100%. In one embodiment, predominantly refers to about 50%-98%, 55%-98%, 60%-98%, 70%-98%, 50%-95%, 55%-95%, 60%-95%, or 70%-95%. For example, "having an isotope predominantly at the bis-allylic site" means the amount of isotopic modification at the bis-allylic site is more than about 40%, 45%, 50%, 55%, 60%, 65%, 70%, 75%, 80%, 85%, 90%, 95% or 100%. In another embodiment, "having an isotope predominantly at one or more allylic site" means the amount of isotopic modification at the allylic site is more than about 40%, 45%, 50%, 55%, 60%, 65%, 70%, 75%, 80%, 85%, 90%, 95% or 100%.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The process of deuteration (or H/D exchange), which involves hydrogen ($^1$H) substitution with its heavier isotope deuterium ($^2$H or D), can be applied in nuclear magnetic resonance (NMR) spectroscopy, mass spectrometry, polymer science, etc. Additionally, selective deuteration can be a tool in pharmaceutical industry regarding drug design, development and discovery because metabolic pathway(s) of a certain pharmaceutical could be dramatically affected by H/D exchange. This can then be used to, for instance, reduce the administered dosage because the biological half-life of a drug could be extended. Furthermore, certain drugs and biological molecules are also confronted by degrading metabolic pathways leading to ruinous side effects that could be averted by a specific H/D exchange process. For example, skin rush and hepatotoxicity in humans caused by Nevirpine (Viramune®), used for the treatment of HIV infection, can be lessened with selective deuteration of this drug. The harmful metabolic pathway(s) of polyunsaturated fatty acids (PUFAs), molecules found in membranes of every cells and a few organelles (subcellular parts), are associated with numerous neurological diseases such as Parkinson's, Alzheimer's, Friedreich's ataxia, etc. The deleterious metabolic pathways in PUFAs are usually induced by radical-based molecules (radicals contain free electrons), which are constantly produced during the normal cellular oxygen consumption process. These very reactive radical species then attack and cleave specific C—H bonds in PUFAs causing irreparable damage to these biological molecules, which could be prevented by selective H/D or H/T exchange. A drug based on a selectively deuterated PUFA, which was previously shown to have no serious side effects, can be used for treatment of Friedreich's ataxia. For many other potential pharmaceuticals, selective deuteration of PUFAs at the target bis-allylic (a $CH_2$ group found between two alkene fragments), positions has been limited to extensive synthetic procedures (or full syntheses) that might not be financially and practically viable at the industrial scale. Therefore, development of a selective and catalytic H/D or H/T exchange process, preferentially performed by a transition metal-based complex, would be enormously valuable for further exploration and commercial viability of these biologically important molecules.

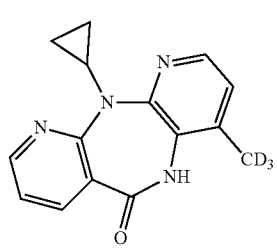

Deuterated Nevirapine

The transition metal based catalysts and other agents for use in the method described herein can include catalysts and agents described in J. W. Faller, H. Felkin, *Organometallics* 1985, 4, 1487; J. W. Faller, C. J. Smart, *Organometallics* 1989, 8, 602; B. Rybtchinski, R. Cohen, Y. Ben-David, J. M. L. Martin, D. Milstein, *J. Am. Chem. Soc.* 2003, 125, 11041; R. Corberán, M. Sanaú, E. Peris, *J. Am. Chem. Soc.* 2006, 128, 3974; S. K. S. Tse, P. Xue, Z. Lin, G. Jia, *Adv. Synth. Catal.* 2010, 352, 1512; A. Di Giuseppe, R. Castarlenas, J. J. Pérez-Torrente, F. J. Lahoz, V. Polo, L. A. Oro, *Angew. Chem. Int. Ed.* 2011, 50, 3938; M. Hatano, T. Nishimura, H. Yorimitsu, *Org. Lett.* 2016, 18, 3674; S. H. Lee, S. I. Gorelsky, G. I. Nikonov, *Organometallics* 2013, 32, 6599; G. Erdogan and D. B. Grotjahn, *J. Am. Chem. Soc.* 2009, 131, 10354; G. Erdogan and D. B. Grotjahn, *Top Catal.* 2010, 53, 1055; M. Yung, M. B. Skaddan, R. G. Bergman, *J. Am. Chem. Soc.* 2004, 126, 13033; M. H. G. Prechtl, M. Holscher, Y. Ben-David, N. Theyssen, R. Loschen, D. Milstein, W. Leitner, *Angew. Chem. Int. Ed.* 2007, 46, 2269; T. Kurita, K. Hattori, S. Seki, T. Mizumoto, F. Aoki, Y. Yamada, K. Ikawa, T. Maegawa, Y. Monguchi, H. Sajiki, *Chem. Eur. J.* 2008, 14, 664; Y. Feng, B. Jiang, P. A. Boyle, E. A. Ison, *Organometallics* 2010, 29, 2857; S. K. S. Tse, P. Xue, C. W. S. Lau, H. H. Y. Sung, I. D. Williams, G. Jia, *Chem. Eur. J.* 2011, 17, 13918; E. Khaskin, D. Milstein, *ACS Catal.* 2013, 3, 448; each of which is incorporated by reference herein in its entirety.

Additional suitable transitional metal catalysts can include those catalysts described in D. B. Grotjahn, C. R. Larsen, J. L. Gustafson, R. Nair, A. Sharma, *J. Am. Chem. Soc.* 2007, 129, 9592; J. Tao, F. Sun, T. Fang, *J. Organomet. Chem.* 2012, 698, 1; Atzrodt, V. Derdau, T. Fey, J. Zimmermann, *Angew. Chem. Int. Ed.* 2007, 46, 7744. b) T. Junk, W. J. Catallo, *Chem. Soc. Rev.* 1997, 26, 401; L. Neubert, D. Michalik, S. Bahn, S. Imm, H. Neumann, J. Atzrodt, V. Derdau, W. Holla, M. Beller, *J. Am. Chem. Soc.* 2012, 134, 12239; T. G. Grant, *J. Med. Chem.* 2014, 57, 3595; R. P. Yu, D. Hesk, N. Rivera, I. Pelczer, P. J. Chirik, *Nature* 2016, 529, 195; all of which are incorporated by reference herein in their interties.

Linoleic acid, the omega-6 essential PUFA that gives rise to higher homologs such as arachidonic acid, has been successfully prepared as an 11,11-D2-derivative by a 6-step synthesis (U.S. patent application Ser. No. 12/916,347). Methods for the synthesis of isotopically modified 1,4-dienes such as PUFAs are described herein.

Synthesis of Isotopically Modified 1,4-Dienes:

Preparation of isotopically modified 1,4-diene systems at the bis-allylic position from non-modified 1,4-diene systems via a "direct exchange" synthetic route represents an efficient method for the preparation of compounds with isotopic modification at the bis-allylic position. However, abstracting the bis-allylic hydrogen with base, quenching the resulting radical with $D_2O$, and then repeating the process to replace the second bis-allylic hydrogen will inevitably lead to a double bond shift due to an intrinsic propensity of 1,4-diene systems to rearrange into conjugated 1,3-dienes upon hydrogen abstraction from the bis-allylic position. A 'softer' method, one that does not result in double bond rearrangement, is therefore required.

Some transition metals are known to weaken C—H (carbon-hydrogen) bonds. For example, platinum complexes can insert a platinum atom into a C—H bond. The resultant organometallic compound is then amenable to subsequent derivization to afford an isotopically labeled compound. However, the use of platinum as a transition metal, such is with a Shilov system (*Chem. Rev.* 1997, 97(8), 2879-2932) may not be directly applicable to certain compounds, such as PUFAs because (1) the Shilov system preferentially activates stronger C—H bonds over weaker C—H bonds, and (2) the platinum complexes are reactive towards double bonds.

In some embodiments, a direct exchange method affords a 1,4-diene system that is isotopically modified with one or more deuterium atoms and/or one of more tritium atoms at a bis-allylic position. Such an embodiment is represented in FIG. 1, where $R^1$, $R^2$, $R^3$, and $R^4$ are any one or more of $C_a$-$C_b$ alkyl, $C_a$-$C_b$ alkenyl, $C_a$-$C_b$ alkynyl, $C_a$-$C_b$ cycloalkyl, $C_a$-$C_b$ cycloalkenyl, $C_a$-$C_b$ cycloalkynyl, $C_a$-$C_b$ carbocyclyl, $C_a$-$C_b$ heterocyclyl, $C_a$-$C_b$ heteroaryl, $C_a$-$C_b$ heteroalicyclic, $C_a$-$C_b$ aralkyl, $C_a$-$C_b$ heteroaralkyl, $C_a$-$C_b$ heteroalicyclyl(alkyl), or a $C_a$-$C_b$ lower alkylene group, wherein "a" and "b" of the $C_a$-$C_b$ is any one or more of 1, 2, 3, 4, 5, 6, 7, 8, 9, 10, 11, 12, 13, 14, 15, 16, 17, 18, 19, 20, and Y is either deuterium or tritium. Each of $R^1$, $R^2$, $R^3$, and $R^4$ can be independently substituted or unsubstituted.

In some embodiments, the bis-allylic position of a 1,4-diene system is isotopically modified by treatment with a transition metal and an isotope source. In other embodiments, the transition metal is any one or more of Rhodium, Iridium, Nickel, Platinum, Palladium, Aluminum, Titanium, Zirconium, Hafnium, or Ruthenium. In other embodiments the transition metal is a rhodium(II) metal or a ruthenium(III) metal. In other embodiments, the transition metal is dirhodium (II) or ruthenium(III) and a ligand is utilized. In other embodiments, the transition metal and ligand is a dirhodium (II) caprolactamate complex or a ruthenium(III) chloride complex. In some embodiments, the transition metal is used in catalytic amounts. In other embodiments, the transition metal is used in stoichiometric amounts. In some embodiments, a co-catalyst is used. In some embodiments, the isotope source is a source of $D^-$ or $T^-$. In other embodiments, the isotope source is tributyltin deuteride.

Figure 2:
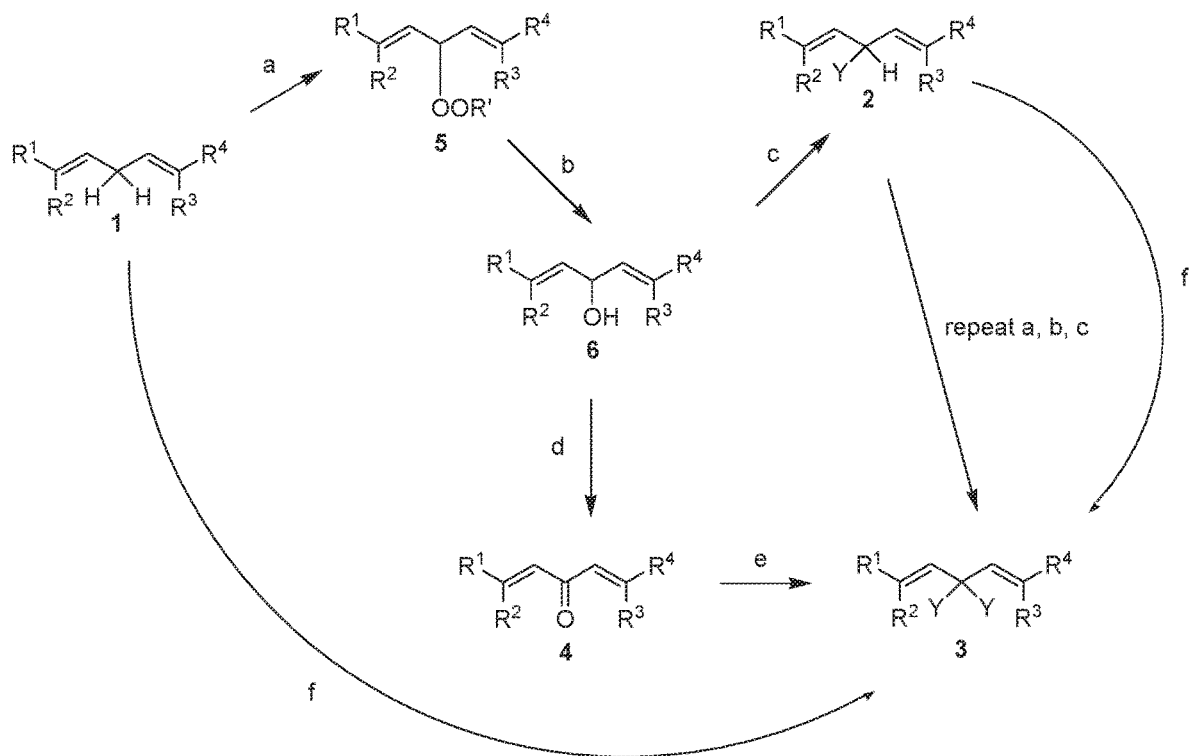

In some embodiments, the synthetic route in FIG. 2 from a compound of Formula 1 to compounds of Formulas 2 and 3 and/or a compound of Formula 2 to a compound of Formula 3 involves proceeding through intermediates such as compounds of Formulas 4-6, wherein $R^1$ is independently selected from $C_a$-$C_b$ alkyl, $C_a$-$C_b$ alkenyl, $C_a$-$C_b$ alkynyl, $C_a$-$C_b$ cycloalkyl, $C_a$-$C_b$ cycloalkenyl, $C_a$-$C_b$ cycloalkynyl, $C_a$-$C_b$ carbocyclyl, $C_a$-$C_b$ heterocyclyl, $C_a$-$C_b$ heteroaryl, $C_a$-$C_b$ heteroalicyclic, $C_a$-$C_b$ aralkyl, $C_a$-$C_b$ heteroaralkyl, $C_a$-$C_b$ heteroalicyclyl(alkyl), or a $C_a$-$C_b$ lower alkylene group, wherein "a" and "b" of the $C_a$-$C_b$ is any one or more of 1, 2, 3, 4, 5, 6, 7, 8, 9, 10, 11, 12, 13, 14, 15, 16, 17, 18, 19, 20. Such embodiments are schematically represented in FIG. 2 with $R^1$, $R^2$, $R^3$, $R^4$, and Y having been previously defined.

In reaction (a) of FIG. 2, an adaptation of a method termed "allylic oxidation" is employed to afford a compound of Formula 5 from a compound of Formula 1 (See Catino A J et al, JACS 2004; 126:13622; Choi H. et al *Org. Lett.* 2007; 9:5349; and U.S. Pat. No. 6,369,247, the disclosures of which are hereby incorporated by reference in their entirety). Oxidation of a compound of Formula 1 in the presence of a transition metal and an organic peroxide readily affords an organic peroxide of Formula 5. In some embodiments, the transition metal is any one or more of Rhodium, Iridium, Nickel, Platinum, Palladium, Aluminum, Titanium, Zirconium, Hafnium, or Ruthenium. In other embodiments the transition metal is a rhodium(II) metal or a ruthenium(III) metal. In other embodiments, the transition metal is dirhodium (II) or ruthenium(III) and a ligand is utilized. In other embodiments, the transition metal and ligand is a dirhodium (II) caprolactamate complex or a ruthenium(III) chloride complex. In some embodiments, the transition metal is used in catalytic amounts. In other embodiments, the transition metal is used in stoichiometric amounts.

Many organic peroxides can be used in the embodiments described herein. In some embodiments, these organic peroxides include $C_a$-$C_b$ alkyl peroxides, $C_a$-$C_b$ alkenyl peroxides, $C_a$-$C_b$ alkynyl peroxides, $C_a$-$C_b$ cycloalkyl peroxides, $C_a$-$C_b$ cycloalkenyl peroxides, $C_a$-$C_b$ cycloalkynyl peroxides, $C_a$-$C_b$ carbocyclyl peroxides, $C_a$-$C_b$ heterocyclyl peroxides, $C_a$-$C_b$ heteroaryl peroxides, $C_a$-$C_b$ heteroalicyclic peroxides, $C_a$-$C_b$ aralkyl peroxides, $C_a$-$C_b$ heteroaralkyl peroxides, $C_a$-$C_b$ heteroalicyclyl(alkyl) peroxides, or a $C_a$-$C_b$ lower alkylene group peroxides, wherein "a" and "b" of the $C_a$-$C_b$ is any one or more of 1, 2, 3, 4, 5, 6, 7, 8, 9, 10, 11, 12, 13, 14, 15, 16, 17, 18, 19, 20. In other embodiments, the organic peroxide is TBHP.

In FIG. 2, the compound of Formula 5 represents a versatile intermediate for the incorporation of deuterium and/or tritium at the bis-allylic position of the 1,4-diene system. The compound of Formula 5 can be reduced to afford a compound of Formula 6 with an alcohol at the bis-allylic position. Such reductions of organic peroxides can be effected with a variety of conditions that include, but are not limited to hydrogen and a catalyst; $LiAlH_4$, Na in alcohol; Zn in acetic acid; CuCl; phosphines such as triphenyl phosphine and tributyl phosphine; $H_2NCSNH_2$; $NaBH_4$; $SmI_2$; and aluminium amalgam (See, e.g., Comprehensive Organic Transformations, $2^{nd}$ Ed., pages 1073-75 and the references cited therein all of which are incorporated herein by reference).

In FIG. 2, the compound of Formula 6 also represents a versatile intermediate for the incorporation of deuterium and/or tritium at the bis-allylic position of the 1,4-diene system. A compound of Formula 6 can be reduced to afford a compound of Formula 2 using multiple methods (reaction c), including, but not limited to, tributyltin deuteride deoxygenation (Watanabe Y et al, *Tet. Let.* 1986; 27:5385); LiBDEt$_3$ (*J. Organomet. Chem.* 1978; 156,1,171; ibid. 1976; 41:18,3064); Zn/NaI (*Tet. Lett.* 1976; 37:3325); DCC (*Ber.* 1974; 107:4,1353); thioacetal (*Tet. Lett.* 1991; 32:49,7187). Repeating the steps described above for reactions a, b, and c in FIG. 2 can be used to transform the mono-isotopically modified compound of Formula 2 into the di-isotopically modified compound of Formula 3.

Alternatively, the compound of Formula 6 can be or further oxidized to afford a compound of Formula 4 with a bis-allylic carbonyl group (reaction d). Such oxidations can be effected with a variety of conditions (See, e.g., Comprehensive Organic Transformations, $2^{nd}$ Ed., pages 1234-1250 and the references cited therein all of which are incorporated herein by reference). The carbonyl group present in the compound of Formula 4 can be further reduced to the deuteromethylene group, —$CD_2$-, using various reaction conditions, that include, but are not limited to, the Wolff-Kishner reaction (See, e.g., Furrow M E et al., *JACS* 2004; 126:5436 which is incorporated herein by reference).

Transition metals can also be employed to directly address the bis-allylic site of a 1,4-diene system such as the system present in compounds of Formulas 1 and 2 above. Such a use of transition metals is represented by reaction f of FIG. 2. The use of such transition metals can involve the formation of a pi-allylic complex and concomitant insertion of an isotope such as deuterium and/or tritium without re-arrangement of the double bonds. Embodiments of this process are represented in FIG. 3.

Figure 3:
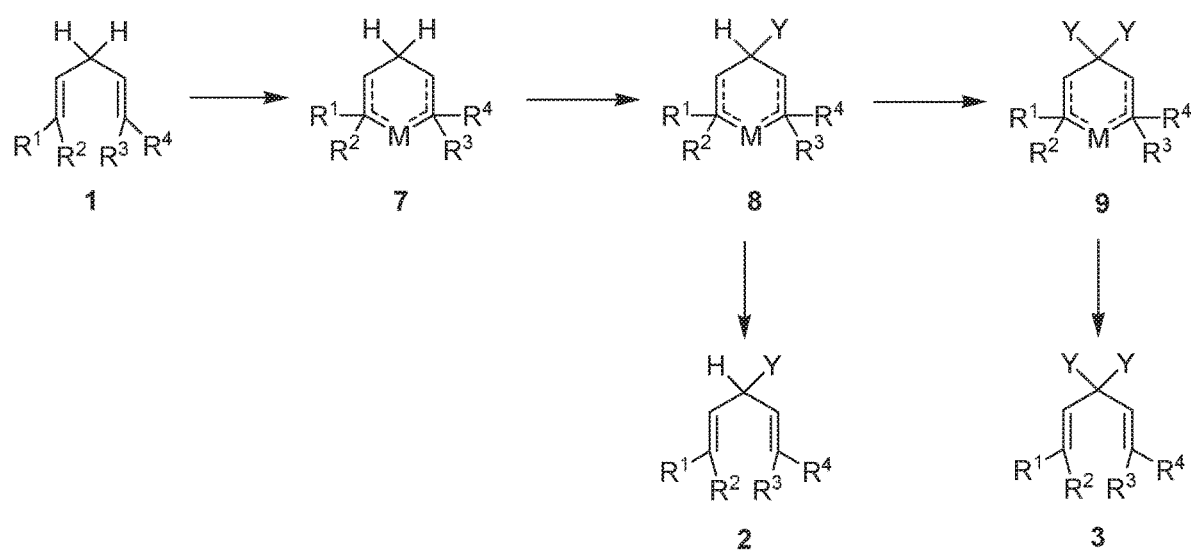
FIG. 3. is a schematic representation of the use of pi-allylic complexes and concomitant insertion of one or more isotopes to prepare isotopically modified 1,4-diene systems.

In FIG. 3, transition metal complexes such as compounds of Formula 7, including deuterium atom(s)-containing transition metal complexes such as compounds of Formulas 8 and 9, assist in folding this 1,4-diene fragment into a six-membered ring system. The bis-allylic methylene at the top of the six-membered structure can then be deuterated by analogy with the well-known process of deuterium scrambling in benzene. In some embodiments, M is any one or more of Rhodium, Iridium, Nickel, Platinum, Palladium, Aluminum, Titanium, Zirconium, Hafnium, or Ruthenium. In other embodiments M is a rhodium(II) metal or a ruthenium(III) metal. In other embodiments, M is dirhodium (II) or ruthenium(III) and a ligand is utilized. In other embodiments, M is a dirhodium (II) caprolactamate complex or a ruthenium(III) chloride complex. In FIG. 3, $R^1$, $R^2$, $R^3$, $R^4$, and Y are as defined above.

Synthesis of Isotopically Modified PUFAs:

Preparation of isotopically modified PUFAs from non-modified PUFAs via a "direct exchange" synthetic route can be accomplished as described above in FIGS. 1-3. In some embodiments, compounds of Formula 1 are selected from any one or more of the following compounds:

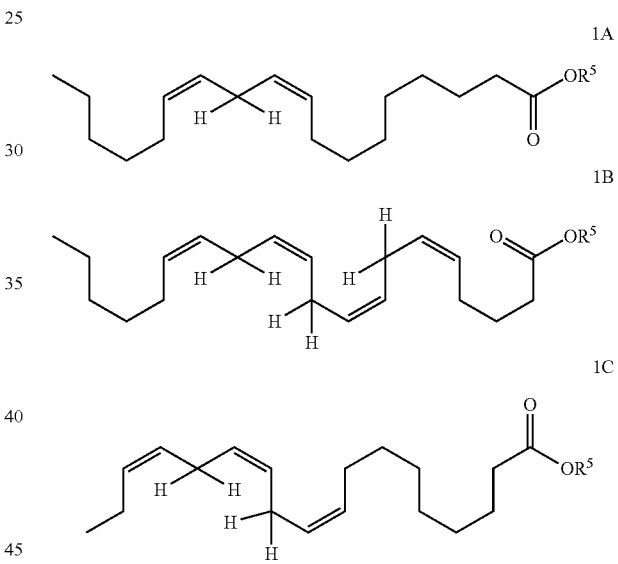

In the compounds of Formulas 1A-1C, $R^5$ is a $C_a$-$C_b$ alkyl, $C_a$-$C_b$ alkenyl, $C_a$-$C_b$ alkynyl, $C_a$-$C_b$ cycloalkyl, $C_a$-$C_b$ cycloalkenyl, $C_a$-$C_b$ cycloalkynyl, $C_a$-$C_b$ carbocyclyl, $C_a$-$C_b$ heterocyclyl, $C_a$-$C_b$ heteroaryl, $C_a$-$C_b$ heteroalicyclic, $C_a$-$C_b$ aralkyl, $C_a$-$C_b$ heteroaralkyl, $C_a$-$C_b$ heteroalicyclyl(alkyl), or a $C_a$-$C_b$ lower alkylene group, wherein "a" and "b" of the $C_a$-$C_b$ is any one or more of 1, 2, 3, 4, 5, 6, 7, 8, 9, 10, 11, 12, 13, 14, 15, 16, 17, 18, 19, 20. In some embodiments, $R^5$ is a $C_a$-$C_b$ alkyl group wherein "a" and "b" of the $C_a$-$C_b$ is any one or more of 1, 2, 3, 4, or 5.

In some embodiments, compounds of Formula 2 are selected from any one or more of the following compounds:

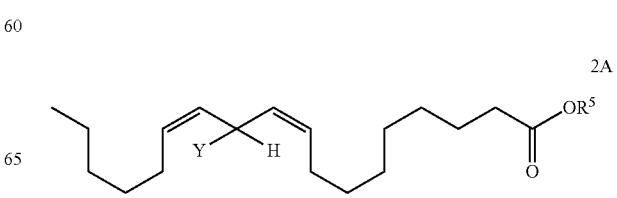

2B

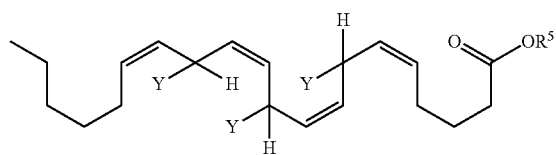

2C

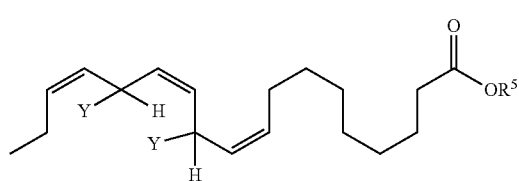

In the compounds of Formulas 2A-2C, Y and $R^5$ are as previously defined.

In some embodiments compounds of Formula 3 are selected from any one or more of the following compounds:

3A

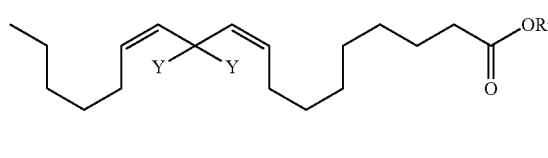

3B

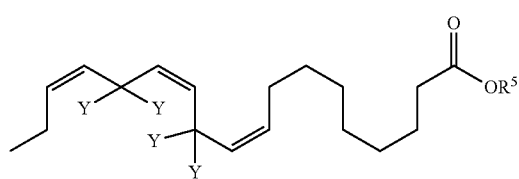

3C

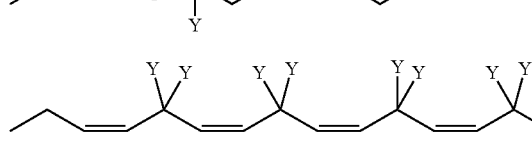

3D

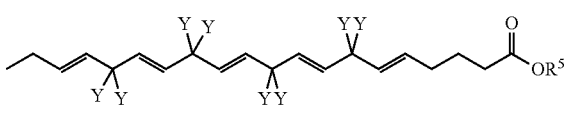

3E

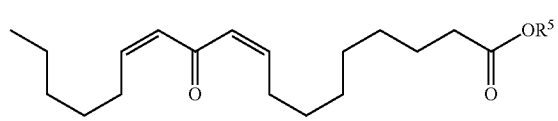

In the compounds of Formulas 3A-3E, Y and $R^5$ are as previously defined.

In some embodiments, compounds of Formula 4 are selected from any one or more of the following compounds:

4A

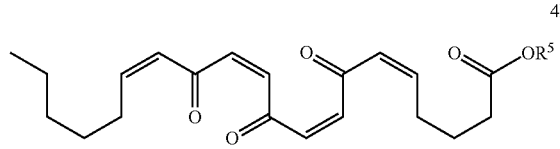

4B

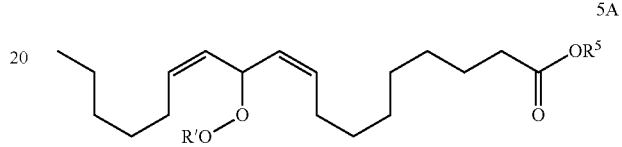

4C

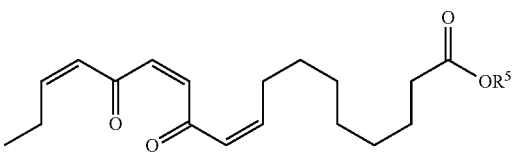

In the compounds of Formulas 4A-4C, $R^5$ is as previously defined.

In some embodiments, compounds of Formula 5 are selected from any one or more of the following compounds:

5A

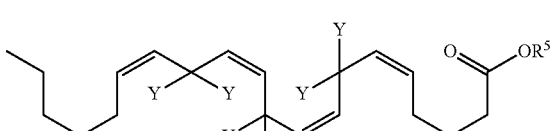

5B

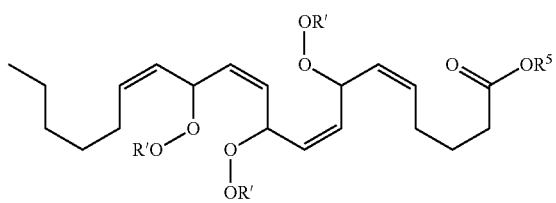

5C

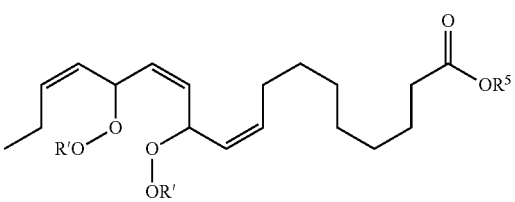

In the compounds of Formulas 5A-5C, $R^1$ and $R^5$ are as previously defined.

In some embodiments, compounds of Formula 6 are selected from any one or more of the following compounds:

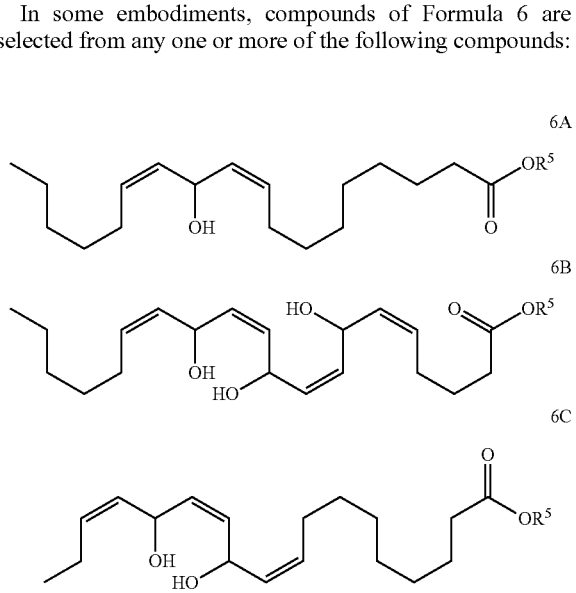

In the compounds of Formulas 6A-6C, $R^5$ is as previously defined.

In some embodiments, compounds of Formula 7 are selected from any one or more of the following compounds:

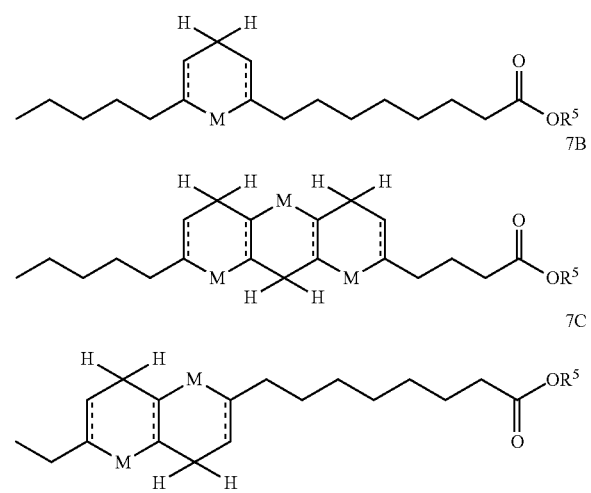

In the compounds of Formulas 7A-7C, M and $R^5$ are as previously defined.

In some embodiments, compounds of Formula 8 are selected from any one or more of the following compounds:

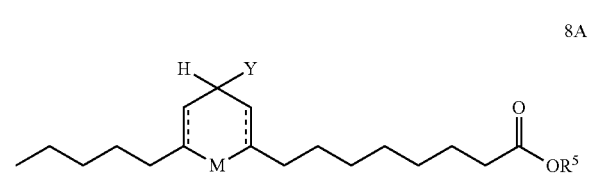

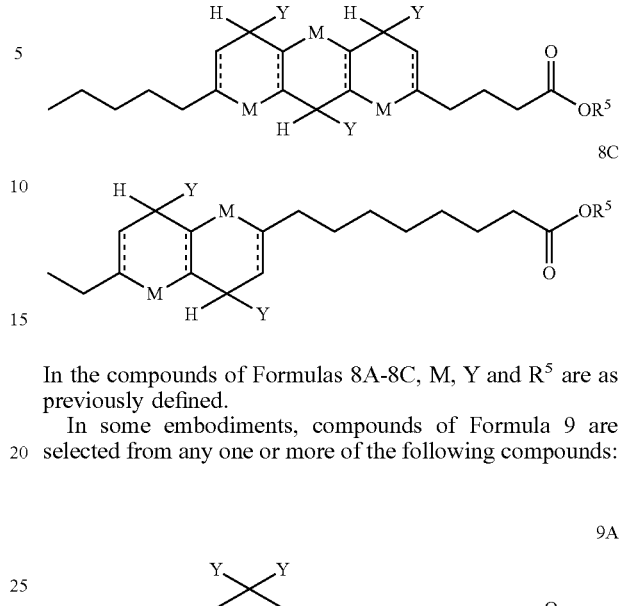

In the compounds of Formulas 8A-8C, M, Y and $R^5$ are as previously defined.

In some embodiments, compounds of Formula 9 are selected from any one or more of the following compounds:

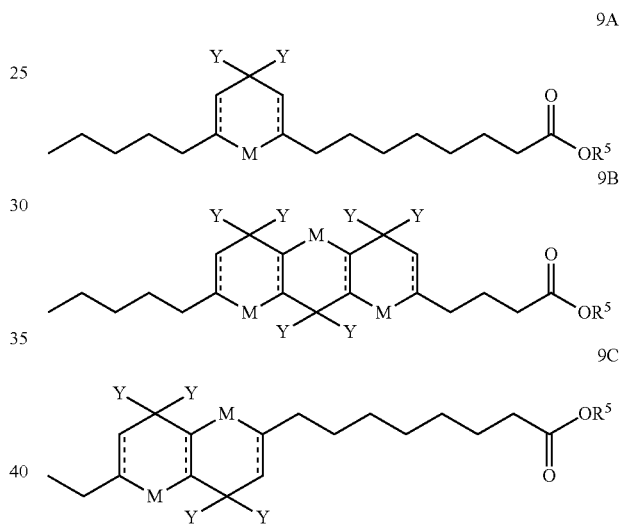

In the compounds of Formulas 9A-9C, M, Y and $R^5$ are as previously defined.

Method of Site-Specific Isotopic Modification

D-PUFAs can be manufactured by total synthesis, whereby simple fragments are chemically assembled in a step by step fashion to yield the desired derivatives. The simple D-PUFA, D2-linoleic acid (D2-Lin), can be made using this approach. However, with increasing number of double bonds, the synthesis becomes more complex and expensive, giving lower yields and higher levels of impurities. D-PUFAs with the double bond number higher than 2, such as linolenic (LNN), arachidonic (ARA), eicosapentaenoic (EPA) and decosahexaenoic (DHA) are increasingly difficult to produce. A synthetic method that does not require a purification step is highly desirable. But for the number of double bonds higher than 2, the D-PUFAs would require an expensive and time consuming chromatographic purification step. For D-PUFAs with the number of double bonds exceeding 4, the purification based on silver nitrate impregnated silica gel chromatography is increasingly inefficient, rendering the total synthesis manufacturing approach essentially inadequate. The methods described herein not only achieves a selective and efficient isotopic modification with fewer reaction steps but also avoids expensive and time-consuming purification steps.

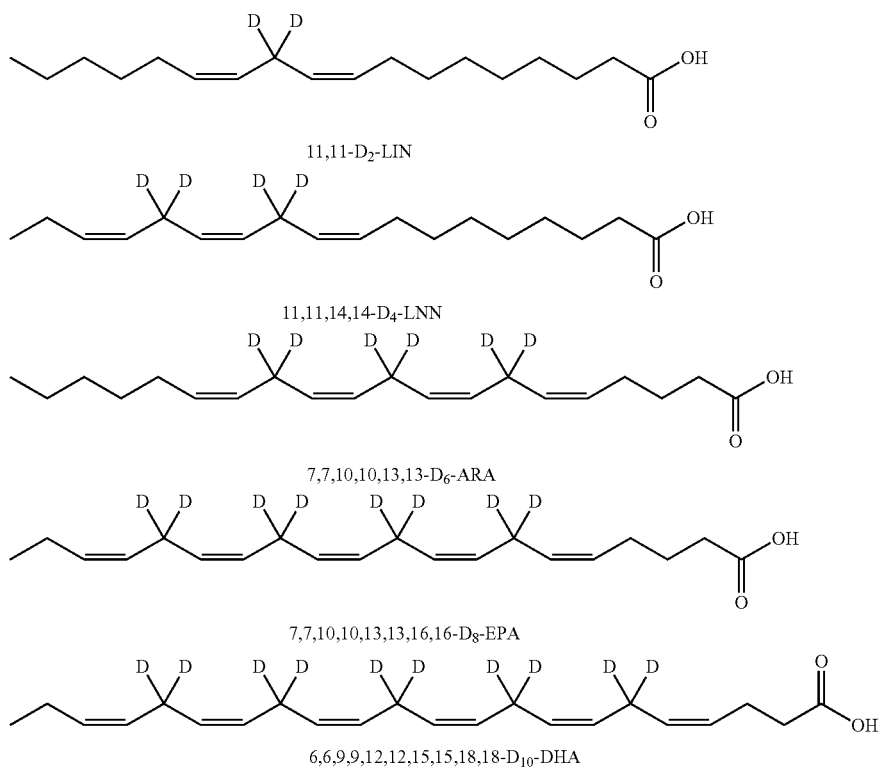

Conventional deuteration of molecules containing one alkene using the transition metal as a catalyst often have problems, including that predominantly vinylic positions (hydrogen atom connected to a doubly bonded carbon atom) are selectively deuterated. Many alkenes contain movement-restricted double bonds. Limited examples of linear (movement-unrestricted) alkenes yielded positional isomers, and cis-to-trans isomerisation always accompanied the deuteration process and lack of any reports on H/D exchange involving polyunsaturated alkenes. Without wishing to be bound by any theory, it is believed that some catalytic systems are not adequate for the target H/D exchange at the bis-allylic positions of PUFAs because the double bonds of these molecules are not only in the cis configuration but they are also separated by a methylene group (i.e. bis-allylic positon; FIG. 1). This particular alkene arrangement is less thermodynamically favoured than a system that would contain all trans-bonds in a conjugated configuration. Without wishing to be bound by any theory, it is believed that if a catalytic system is to perform selective deuteration at the bis-allylic positions through any of the already described mechanisms, the polyalkenes "falling" into these thermodynamic sinks/traps need to be prevented; otherwise, the target H/D exchange would need to be conducted through a new isotopic modification mechanism. Selective and efficient deuteration of various polyalkenes (including PUFAs) at the bis-allylic sites by a commercially available Ru-based complex using the least expensive deuterium source $D_2O$ can be achieved through the methods described herein. The isotopic modification described herein can occur in the absence of the thermodynamic side products (trans-isomers and conjugated alkenes) with a completely different mechanism from the ones already established for deuteration of various organic substrate.

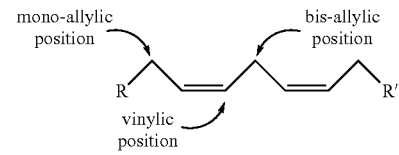

The methods described herein can be employed to achieve selective and efficient isotopic modification (e.g., D or T) of various polyunsaturated lipids (including PUFAs) at the bis-allylic sites by a transitional metal based catalyst (e.g., Ru-based complex) using an easily available isotopic modification agent (e.g., $D_2O$ as the deuterium source). The isotopic modification, such as the H/D exchange, can occur in the absence of the thermodynamic side products (trans-isomers and conjugated alkenes).

In addition, the methods described herein can be employed to perform selective isotopic modification of a mixture of polyunsaturated lipids (e.g., PUFA or PUFA esters) without having to separate the polyunsaturated lipids prior to reaction.

Figure 5:
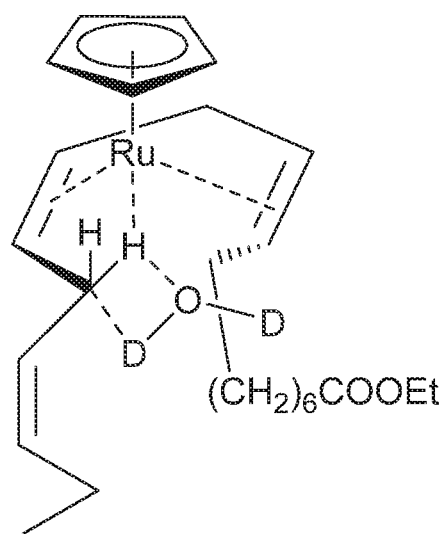
FIG. 5 shows an intermediate in the deuteration reaction at a bis-allylic position of ethyl linolenate (E-lnn).

As described herein, the transition metal based catalysts (e.g. Ru based catalysts) can deuterate or tritiate bis-allylic positions of the systems with three or more double bonds (e.g., E-Lnn, E-Ara, E-DHA, etc.) and cause no cis-trans isomerization or alkene conjugation in the polyunsaturated lipid. An intermediate for the deuteration of a bis-allylic position of E-Lnn is shown in FIG. 5.

The methods described herein can be employed to obtain polyunsaturated lipid selectively deuterated or tritiated at one or more allylic positions. In some embodiments, the method described herein can yield a mixture of polyunsaturated lipid deuterated or tritiated at one or more allylic positions.

A catalytic H/D exchange at the bis-allylic sites, starting directly from non-deuterated, "natural" PUFAs, is achieved using the methods described herein. The synthesis methods described herein can solve both thermodynamic and selectivity challenges. PUFA's double bonds are not only in cis configuration but they are also separated by a methylene group (i.e. bis-allylic positons, or skipped diene) which is less thermodynamically favoured than a system that would contain all trans bonds in a conjugated configuration. In addition, distinguishing between mono- and bis-allylic positions might be difficult if the mechanism for the target H/D exchange may require the formation of an allyl intermediate.

The methods described herein result in site-specific deuteration of polyunsaturated lipid, wherein the deuteration occurs at mon-allylic and bis-allylic positions. For polyunsaturated lipid having three or more double bonds, the method described herein can result in deuteration occurring predominantly at the bis-allylic positions.

Some embodiments relate to a method for site-specifically modifying a polyunsaturated lipid with an isotope, comprising: reacting a polyunsaturated lipid with an isotope-containing agent in a presence of a transition metal-based catalyst, whereby an isotopically-modified polyunsaturated lipid having the isotope at one or more mono-allylic or bis-allylic sites is obtained, wherein the isotope-containing agent comprises at least one isotope selected from the group consisting of deuterium, tritium, and combinations thereof.

In some embodiments, the polyunsaturated lipid is selected from the group consisting of a fatty acid, fatty acid ester, fatty acid thioester, fatty acid amide, fatty acid mimetic, and fatty acid prodrug. In some embodiments, the polyunsaturated lipid is selected from the group consisting of a fatty acid, fatty acid ester, fatty acid thioester and fatty acid amide. In some embodiments, the polyunsaturated lipid is a fatty acid or fatty acid ester.

Polyunsaturated lipid having multiple double bonds can be isotopically modified using the methods described herein. In some embodiments, the polyunsaturated lipid has two or more carbon-carbon double bonds. In some embodiments, the polyunsaturated lipid has three or more carbon-carbon double bonds.

In some embodiments, the polyunsaturated fatty acid has a structure according to Formula (IA):

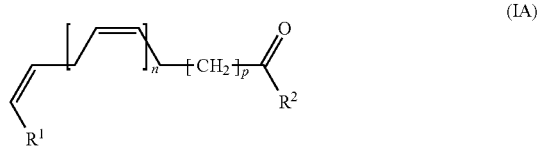

(IA)

wherein:

$R^1$ is selected from the group consisting of H and $C_{1-10}$ alkyl;

$R^2$ is selected from the group consisting of —OH, —OR$^3$, —SR$^3$, phosphate, and —N(R$^3$)$_2$;

each $R^3$ is independently selected from the group consisting of $C_{1-10}$ alkyl, $C_{2-10}$ alkene, $C_{2-10}$ alkyne, $C_{3-10}$ cycloalkyl, $C_{6-10}$ aryl, 4-10 membered heteroaryl, and 3-10 membered heterocyclic ring, wherein each $R^3$ is substituted or unsubstituted;

n is an integer of from 1 to 10; and p is an integer of from 1 to 10.

In some embodiments, the polyunsaturated lipid is selected from the group consisting of omega-3 fatty acid, omega-6 fatty acid, and omega-9 fatty acid. In some embodiments, the polyunsaturated lipid is an omega-3 fatty acid. In some embodiments, the polyunsaturated lipid is an omega-6 fatty acid. In some embodiments, the polyunsaturated lipid is an omega-9 fatty acid.

In some embodiments, the polyunsaturated lipid is selected from the group consisting of linoleic acid and linolenic acid. In some embodiments, the polyunsaturated lipid is a linoleic acid. In some embodiments, the polyunsaturated lipid is a linolenic acid.

In some embodiments, the polyunsaturated lipid is selected from the group consisting of gamma linolenic acid, dihomo gamma linolenic acid, arachidonic acid, and docosatetraenoic acid.

In some embodiments, the polyunsaturated fatty acid ester is selected from the group consisting of a triglyceride, a diglyceride, and a monoglyceride.

In some embodiments, the fatty acid ester is an ethyl ester.

In some embodiments, the isotopically-modified polyunsaturated lipid is a deuterated polyunsaturated lipid having deuterium at one or more bis-allylic sites.

In some embodiments, the isotopically-modified polyunsaturated lipid is a deuterated polyunsaturated lipid having deuterium at all bis-allylic sites.

In some embodiments, the isotopically-modified polyunsaturated lipid is a deuterated polyunsaturated lipid having deuterium at one or more mono-allylic sites.

In some embodiments, the polyunsaturated lipid have at least one 1,4-diene moiety. In some embodiments, the polyunsaturated lipid have two or more 1,4-diene moieties.

In some embodiments, the isotopically-modified polyunsaturated lipid is a deuterated polyunsaturated lipid having a deuteration degree of more than 20%, 30%, 40%, 50%, 60%, 70%, 80%, 90%, 92%, 95%, 96%, 97%, 98%, or 99% at bis-allylic sites. In some embodiments, the isotopically-modified polyunsaturated lipid is a deuterated polyunsaturated lipid having a deuteration degree of more than 50% at bis-allylic sites. In some embodiments, the isotopically-modified polyunsaturated lipid is a deuterated polyunsaturated lipid having a deuteration degree of more than 90% at bis-allylic sites. In some embodiments, the isotopically-modified polyunsaturated lipid is a deuterated polyunsaturated lipid having a deuteration degree of more than 95% at bis-allylic sites. In some embodiments, the isotopically-modified polyunsaturated lipid is a deuterated polyunsaturated lipid having a deuteration degree in the range of about 50% to about 95% at bis-allylic sites. In some embodiments, the isotopically-modified polyunsaturated lipid is a deuterated polyunsaturated lipid having a deuteration degree in the range of about 80% to about 95% at bis-allylic sites. In some embodiments, the isotopically-modified polyunsaturated lipid is a deuterated polyunsaturated lipid having a deuteration degree in the range of about 80% to about 99% at bis-allylic sites.

In some embodiments, the isotopically-modified polyunsaturated lipid is a deuterated polyunsaturated lipid having a deuteration degree of lower than 80%, 70%, 60%, 50%, 45%, 40%, 35%, 30%, 20%, or 10% at mono-allylic sites. In some embodiments, the isotopically-modified polyunsaturated lipid is a deuterated polyunsaturated lipid having a deuteration degree of lower than 60% at mono-allylic sites. In some embodiments, the isotopically-modified polyunsaturated lipid is a deuterated polyunsaturated lipid having a deuteration degree of lower than 50% at mono-allylic sites. In some embodiments, the isotopically-modified polyunsaturated lipid is a deuterated polyunsaturated lipid having a deuteration degree of lower than 45% at mono-allylic sites.

In some embodiments, the isotopically-modified polyunsaturated lipid is a deuterated polyunsaturated lipid having a deuteration degree of lower than 40% at mono-allylic sites. In some embodiments, the isotopically-modified polyunsaturated lipid is a deuterated polyunsaturated lipid having a deuteration degree of lower than 35% at mono-allylic sites. In some embodiments, the isotopically-modified polyunsaturated lipid is a deuterated polyunsaturated lipid having a deuteration degree of lower than 30% at mono-allylic sites. In some embodiments, the isotopically-modified polyunsaturated lipid is a deuterated polyunsaturated lipid having a deuteration degree of in the range of about 50% to about 20% at mono-allylic sites. In some embodiments, the isotopically-modified polyunsaturated lipid is a deuterated polyunsaturated lipid having a deuteration degree of in the range of about 60% to about 20% at mono-allylic sites.

In some embodiments, the transition metal-based catalyst comprises a transition metal selected from the group consisting of Rhodium, Iridium, Nickel, Platinum, Palladium, Aluminum, Titanium, Zirconium, Hafnium, Ruthenium, and combinations thereof. In some embodiments, the transition metal-based catalyst is a ruthenium catalyst.

In some embodiments, the transition metal-based catalyst has a structure according to Formula (IIA):

$$[ML^1(L^2)_m]Q_n \qquad (IIA)$$

wherein:

M is selected from the group consisting of Rhodium, Iridium, Nickel, Platinum, Palladium, Aluminum, Titanium, Zirconium, Hafnium, and Ruthenium;

$L^1$ is selected from the group consisting of $C_{3-10}$ cycloalkyl, $C_{6-10}$ aryl, 4-10 membered heteroaryl, and 3-10 membered heterocyclic ring, wherein $L^1$ is substituted or unsubstituted;

each $L^2$ is independently selected from the group consisting of amine, imine, carbene, alkene, nitrile, isonitrile, acetonitrile, ether, thioether, phosphine, pyridine, unsubstituted $C_{3-10}$ cycloalkyl, substituted $C_{3-10}$ cycloalkyl, substituted $C_{6-10}$ aryl, substituted 4-10 membered heteroaryl, unsubstituted $C_{6-10}$ aryl, unsubstituted 4-10 membered heteroaryl, substituted 3-10 membered heterocyclic ring, unsubstituted 3-10 membered heterocyclic ring and any combinations thereof;

m is an integer of from 1 to 3,

Q is an anion bearing a single charge, and n is 0 or 1.

In some embodiments, M is Ruthenium.

In some embodiments, $L^1$ is a $C_{3-10}$ cycloalkyl and $L^1$ is substituted or unsubstituted. In some embodiments, $L^1$ is a 4-10 membered heteroaryl and $L^1$ is substituted or unsubstituted. In some embodiments, $L^1$ is an unsubstituted cyclopentadienyl. In some embodiments, $L^1$ is a substituted cyclopentadienyl.

In some embodiments, each $L^2$ is independently selected from the group consisting of amine, nitrile, isonitrile, acetonitrile, ether, thioether, phosphine, imine, carbene, pyridine, substituted $C_{6-10}$ aryl, substituted 4-10 membered heteroaryl, unsubstituted $C_{6-10}$ aryl, unsubstituted 4-10 membered heteroaryl, substituted 3-10 membered heterocyclic ring, and unsubstituted 3-10 membered heterocyclic ring. In some embodiments, each $L^2$ is —NCCH$_3$. In some embodiments, each $L^2$ is independently selected from the group consisting of —NCCH$_3$, P(R$^4$)$_3$, and substituted 4-10 membered heteroaryl, and any combinations thereof. In some embodiments, at least one $L^2$ is —P(R$^4$)$_3$, wherein each R$^4$ is independently selected from the group consisting of hydrogen, $C_{1-15}$ alkyl, $C_{3-8}$ cycloalkyl, 4-10 membered heteroaryl, $C_{6-15}$ aryl, each optionally substituted with $C_{1-15}$ alkyl, $C_{2-15}$ alkene, $C_{2-15}$ alkyne, halogen, OH, cyano, alkoxy, $C_{3-8}$ cycloalkyl, 4-10 membered heteroaryl, and $C_{6-15}$ aryl. In some embodiments, P(R$^4$)$_3$ is P(t-Bu)$_2$(C$_6$H$_5$). In some embodiments, P(R$^4$)$_3$ is 4-(tert-butyl)-2-(diisopropylphosphaneyl)-1H-imidazole. In some embodiments, each $L^2$ is independently acetonitrile or optionally substituted cyclopentadienyl.

In some embodiments, m is 2. In some embodiments, m is 3. In some embodiments, m is 4.

In some embodiments, Q is (PF$_6$)$^-$, Cl$^-$, F$^-$, I$^-$, Br$^-$, ClO$_4^-$ or BF$_4^-$, In some embodiments, Q is (PF$_6$)$^-$.

For the transition metal-based catalysts Formula (IIA) described herein, each $L^2$ can be independently selected from a list of suitable monodentate or multidentate ligands. In some embodiments, each $L^2$ can independently comprise at least two moieties selected from the group consisting of amine, imine, carbene, alkene, nitrile, isonitrile, acetonitrile, ether, thioether, phosphine, pyridine, substituted $C_{6-10}$ aryl, substituted 4-10 membered heteroaryl, unsubstituted $C_{6-10}$ aryl, unsubstituted 4-10 membered heteroaryl, substituted 3-10 membered heterocyclic ring, and unsubstituted 3-10 membered heterocyclic ring. In some embodiments, one $L^2$ can be an amine, one $L^2$ can be a carbene, and one $L^2$ can be an imine. In some embodiments, at least one $L^2$ can have two or three chelating atoms in the ligand. In some embodiments, one $L^2$ in Formula (IIA) can be a ligand having both imine and phosphine moieties and two or more chelating atoms. In some embodiments, one $L^2$ in Formula (IIA) can be a ligand having nitrile, isonitrile, and phosphine moieties and at least three chelating atoms.

In some embodiments, the ruthenium catalyst has a structure selected from the group consisting of:

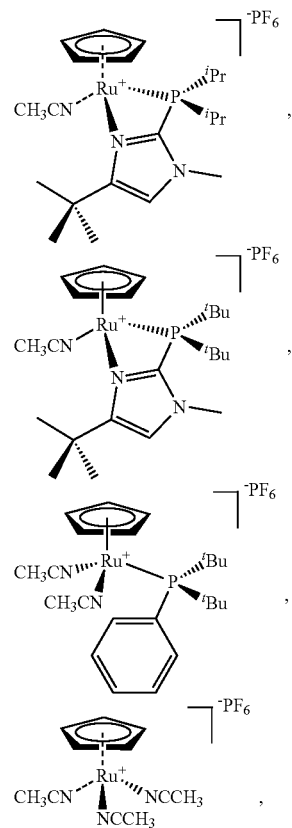

-continued

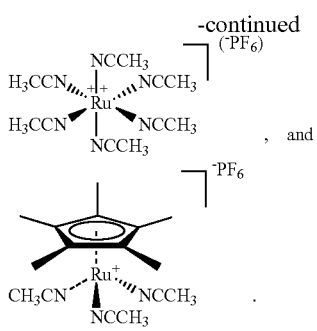

, and

In some embodiments, the ruthenium catalyst has a structure of:

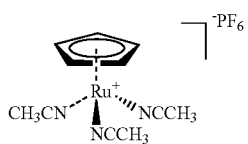

In some embodiments, the transition metal based catalyst has a structure of

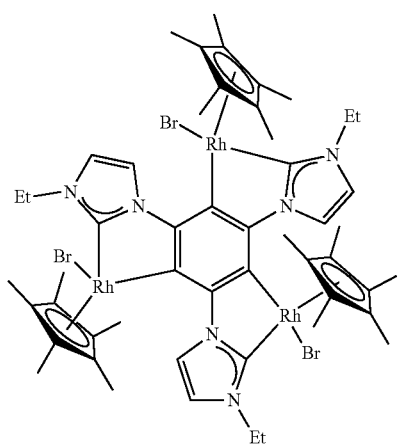

In some embodiments, the ruthenium catalyst has a structure of

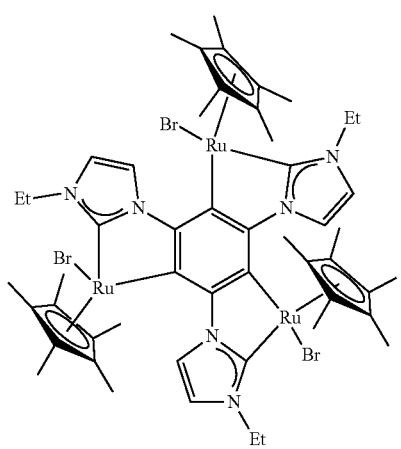

Some embodiments relate to a method for site-specifically modifying a polyunsaturated lipid mixture with an isotope, the method comprising reacting the polyunsaturated lipid mixture with an isotope-containing agent in a presence of a transition metal-based catalyst, whereby an isotopically-modified polyunsaturated lipid mixture having the isotope at one or more mono-allylic or bis-allylic sites is obtained, wherein the isotope-containing agent comprises at least one isotope selected from the group consisting of deuterium, tritium, and combinations thereof.

Compositions

Some embodiments relate to a composition comprising one or more isotopically-modified polyunsaturated lipids having an isotope predominantly at one or more allylic sites, wherein the isotope is selected from the group consisting of deuterium, tritium, and combinations thereof. In some embodiments, the isotope is deuterium. In some embodiments, the isotope is tritium.

In some embodiments, the isotopically modified polyunsaturated lipid is prepared according to the method described herein.

In some embodiments, the isotopically-modified polyunsaturated lipids in the composition described herein are deuterated predominantly at bis-allylic sites. In some embodiments, the isotopically-modified polyunsaturated lipids in the composition described herein are deuterated predominantly at mono-allylic sites. In some embodiments, the composition described herein contains polyunsaturated lipid having two or more carbon-carbon double bonds. In some embodiments, the composition described herein contains polyunsaturated lipid having three or more carbon-carbon double bonds.

Isotopically labeled compounds afforded by the disclosed reaction schemes should have minimal or non-existent effects on important biological processes. For example, the natural abundance of isotopes present in biological substrates implies that low levels of isotopically labeled compounds should have negligible effects on biological processes. Additionally, hydrogen atoms are incorporated into biological substrates from water, and is it known that the consumption of low levels of $D_2O$, or heavy water, does not pose a health threat to humans. See, e.g., "Physiological effect of heavy water." *Elements and isotopes: formation, transformation, distribution*. Dordrecht: Kluwer Acad. Publ. (2003) pp. 111-112 (indicating that a 70 kg person might drink 4.8 liters of heavy water without serious consequences). Moreover, many isotopically labeled compounds are approved by the U.S. Food & Drug Administration for diagnostic and treatment purposes.

Regarding isotopically labels compounds afforded by the disclosed reaction schemes, in some embodiments, deuterium has a natural abundance of roughly 0.0156% of all naturally occurring hydrogen in the oceans on earth. Thus, a 1,4-diene system such as a PUFA having greater that the natural abundance of deuterium may have greater than this level or greater than the natural abundance level of roughly 0.0156% of its hydrogen atoms reinforced with deuterium, such as 0.02%, but preferably about 5%, 10%, 15%, 20%, 25%, 30%, 35%, 40%, 45%, 50%, 65%, 60%, 65%, 70%, 75%, 80%, 85%, 90%, 95%, or 100%, or a range bounded by any two of the aforementioned percentages, of deuterium with respect to one or more hydrogen atoms in each PUFA molecule.

In some embodiments, isotopic purity refers to the percentage of molecules of an isotopically modified 1,4-diene system such as PUFAs in the composition relative to the total number of molecules. For example, the isotopic purity may be about 5%, 10%, 15%, 20%, 25%, 30%, 35%, 40%, 45%, 50%, 65%, 60%, 65%, 70%, 75%, 80%, 85%, 90%, 95%, or 100%, or a range bounded by any two of the aforementioned percentages. In some embodiments, isotopic purity may be from about 50%-99% of the total number of molecules in the composition.

In some embodiments, an isotopically modified compound may contain one deuterium atom, such as when one of the two hydrogens in a methylene group is replaced by deuterium, and thus may be referred to as a "D1" compound. Similarly, an isotopically modified compound may contain two deuterium atoms, such as when the two hydrogens in a methylene group are both replaced by deuterium, and thus may be referred to as a "D2" compound. Similarly, an isotopically modified compound may contain three deuterium atoms and may be referred to as a "D3" compound. Similarly, an isotopically modified compound may contain four deuterium atoms and may be referred to as a "D4" compound. In some embodiments, an isotopically modified compound may contain five deuterium atoms or six deuterium atoms and may be referred to as a "D5" or "D6" compound, respectively.

The number of heavy atoms in a molecule, or the isotopic load, may vary. For example, a molecule with a relatively low isotopic load may contain about 1, 2, 3, 4, 5, or 6 deuterium atoms. A molecule with a moderate isotopic load may contain about 10, 11, 12, 13, 14, 15, 16, 17, 18, 19, or 20 deuterium atoms. In a molecule with a very high load, each hydrogen may be replaced with a deuterium. Thus, the isotopic load refers to the percentage of heavy atoms in each molecule. For example, the isotopic load may be about 5%, 10%, 15%, 20%, 25%, 30%, 35%, 40%, 45%, 50%, 65%, 60%, 65%, 70%, 75%, 80%, 85%, 90%, 95%, or 100%, or a range bounded by any two of the aforementioned percentages, of the number of the same type of atoms in comparison to a molecule with no heavy atoms of the same type (e.g. hydrogen would be the "same type" as deuterium). Unintended side effects are expected to be reduced where there is high isotopic purity in a composition, especially a PUFA composition, but low isotopic load in a given molecule. For example, the metabolic pathways will likely be less affected by using a PUFA composition with high isotopic purity but low isotopic load.

One will readily appreciate that when one of the two hydrogens of a methylene group is replaced with a deuterium atom, the resultant compound may possess a stereocenter. In some embodiments, it may be desirable to use racemic compounds. In other embodiments, it may be desirable to use enantiomerically pure compounds. In additional embodiments, it may be desirable to use diastereomerically pure compounds. In some embodiments, it may be desirable to use mixtures of compounds having enantiomeric excesses and/or diastereomeric excesses of about 5%, 10%, 15%, 20%, 25%, 30%, 35%, 40%, 45%, 50%, 65%, 60%, 65%, 70%, 75%, 80%, 85%, 90%, 95%, or 100%, or a range bounded by any two of the aforementioned percentages. In some embodiments, it may be preferable to utilize stereochemically pure enantiomers and/or diastereomers of embodiments—such as when enzymatic reactions or contacts with chiral molecules are being targeted for attenuating oxidative damage. However, in many circumstances, non-enzymatic processes and/or non-chiral molecules are being targeted for attenuating oxidative damage. In such circumstances, embodiments may be utilized without concern for their stereochemical purity. Moreover, in some embodiments, mixtures of enantiomers and diastereomers may be used even when the compounds are targeting enzymatic reactions and/or chiral molecules for attenuating oxidative damage.

In some aspects, isotopically modified compounds impart an amount of heavy atoms in a particular tissue upon administration. Thus, in some aspects, the amount of heavy molecules will be a particular percentage of the same type of molecules in a tissue. For example, the percentage of heavy molecules may be about 1%, 10%, 20%, 30%, 40%, 50%, 60%, 70%, 80%, 90%, 100%, or a range bounded by the selection of any two of the aforementioned percentages.

EXAMPLES

Example 1. Oxidation of Methyl Linoleate

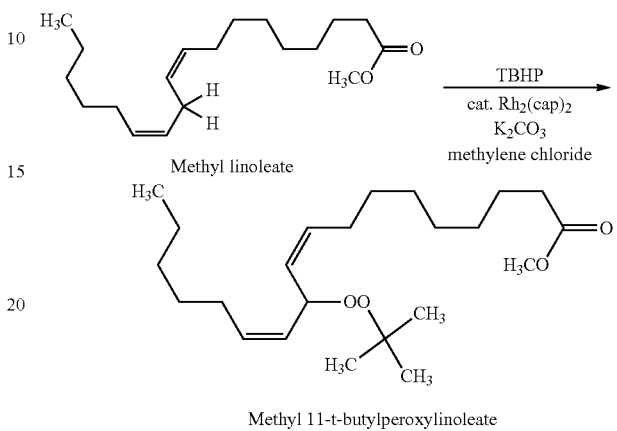

Methyl linoleate (400 mg, 1.36 mmol; 99% purity) was dissolved in 5 mL dry methylene chloride. Potassium carbonate (94 mg, 0.68 mmol) and a small crystal (2 mg) of dirhodium (II) caprolactamate were added and the mixture was allowed to stir to afford a pale purple suspension. Tert-butylhydroperoxide (0.94 mL, 6.8 mmol; 70% aq. solution 7.2 M) was added and the reaction mixture was allowed to stir. TLC (9:1 heptane:ethyl acetate) taken at 45 min showed the absence of starting material ($R_f$=0.51), one major close running spot ($R_f$=0.45), and a number of slower spots. The reaction mixture was allowed to stir in the presence of 15% aqueous sodium sulfite, washed with 12% brine and saturated brine, then dried over sodium sulfate. Filtration and removal of volatiles afforded a yellow substance. Four runs on this scale were combined and chromatographed on a silica gel column (bed=2.4 cm×25 cm). The column was packed with 99:1 heptane:ethyl acetate and eluted with a gradient of 1% to 7% ethyl acetate. The major product of $R_f$=0.45 was isolated as 300 mg of a colorless substance that was substantially pure by TLC and LC/MS. The NMR spectra of this material matched that reported for methyl 11-t-butylperoxylinoleate (Lipids 2000, 35, 947). UV & IR analysis confirmed that the isolated product was not a conjugated diene.

Oxidation of methyl linoleate with TBHP and catalytic ruthenium (III) chloride in heptane/water under the conditions specified in U.S. Pat. No. 6,369,247, example 3, which is incorporated herein by reference, gave essentially the same results as the reaction sequence described above.

Example 2. Synthesis of Isotopically Modified Polyunsaturated Lipid

Various Ru-based complexes were used for selectively performing isotopic modification at the bis-allylic sites. Some of the tested PUFAs have two double bonds and some have three or more double bonds. The reactions had no observable trans isomerisation nor the formation of conjugate configurations.

Figure 4:
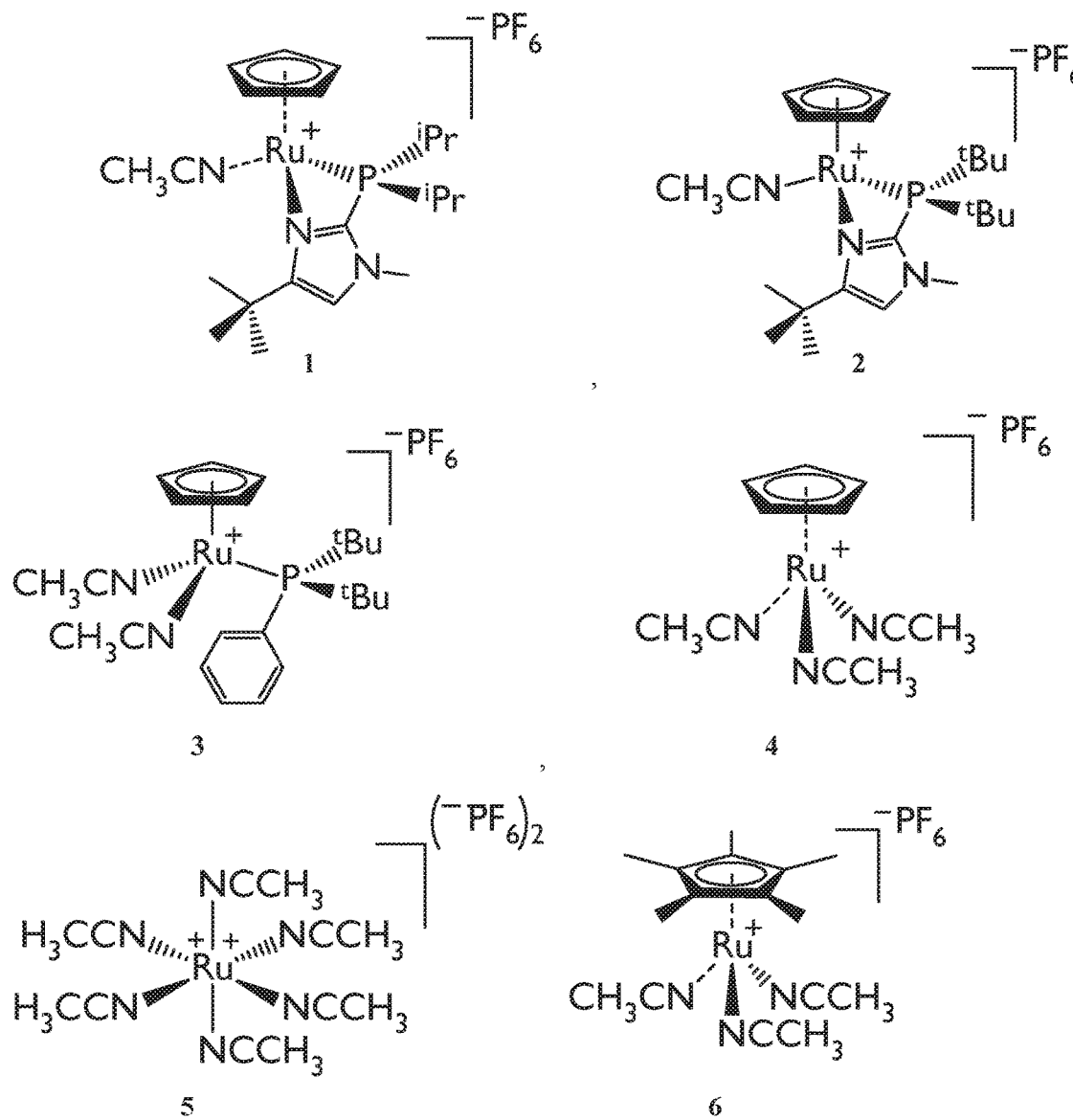
FIG. 4 shows a list of ruthenium based complexes tested for deuteration of the polyunsaturated lipid.

FIG. 4 shows the six Ru based complexes used for the isotopic modification reactions. In FIG. 4, Complex 1 can perform catalytic deuteration at allylic positions of monoalkenes. However, this complex can also be an excellent alkene zipper catalyst capable of moving a double bond across, for up to 30 positions.

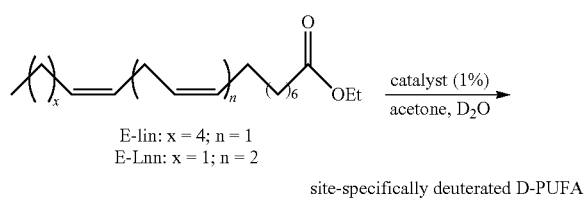

E-lin: x = 4; n = 1
E-Lnn: x = 1; n = 2 site-specifically deuterated D-PUFA

Various Ru complexes (Complex 1-6 in FIG. 4) were tested in the site-specific isotopic modification reaction. In each test, the polyunsaturated lipid was combined with an acetone solution containing each complex, and the reaction mixture immediately proceeded to form of a conjugated system. The results are shown in Table 1 below, which is proceeded by a key including definitions of abbreviations used in the table.

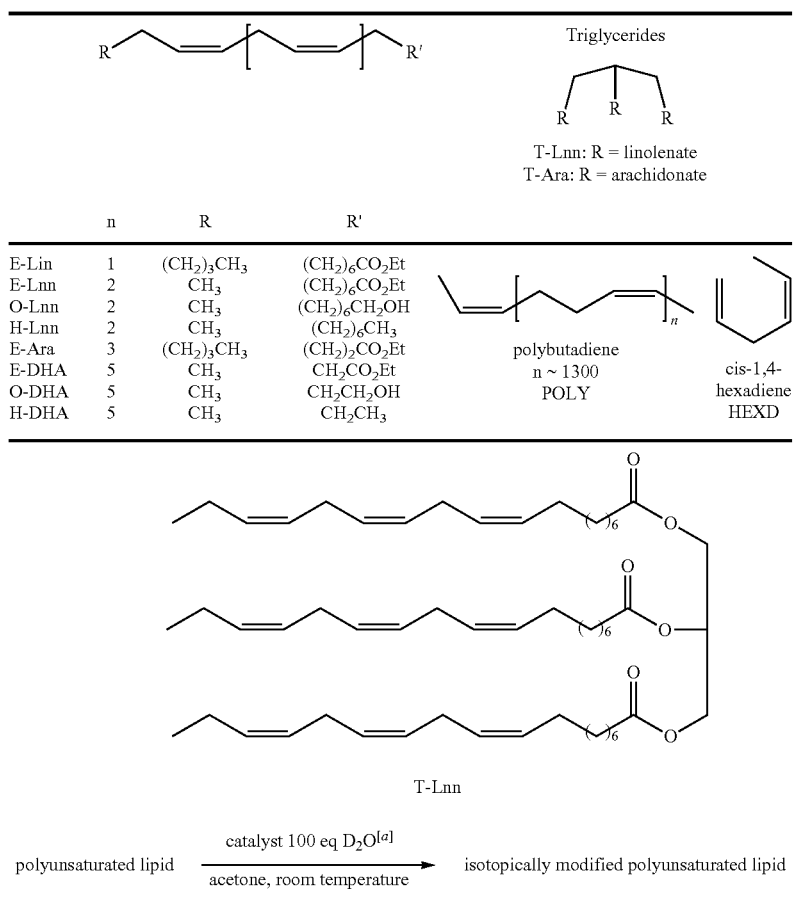

TABLE 1

Deuteration of polyunsaturated lipids with ruthenium complexes shown in FIG. 4.

| # | Complex (%)[b] | Substrate | Double bond conjugation | Time (h) | Yield (%) | Extent of deuteration (%) | |
|---|---|---|---|---|---|---|---|
| | | | | | | Mono-allylic | Bis-allylic |
| 1[c] | 1 (5%) | E-Lin | Yes[d] (82%) | 170 | n.d. | N/A[e] | N/A[e] |
| 2[f] | 2 (5%) | E-Lin | No | 48 | n.i. | 60 | 0 |
| 3[f] | 3 (5%) | E-Lin | No | 24 | n.i | 90 | 0 |
| 4 | 4 (1%) | E-Lin | No | 0.25 | n.i. | 87 | 0 |
| 5 | 4 (1%) | E-Lnn | No | 1 | >99 | 19 (23, 15)[g] | 94 |
| 6 | 4 (1%) | E-Ara | No | 24 | >99 | 13 (15, 10)[g] | 96 |
| 7 | 4 (2%) | E-DHA | No | 18 | >99 | 26 (47, 5)[g] | 96 |

TABLE 1-continued

Deuteration of polyunsaturated lipids with ruthenium complexes shown in FIG. 4.

| # | Complex (%)[b] | Substrate | Double bond conjugation | Time (h) | Yield (%) | Extent of deuteration (%) Mono-allylic | Extent of deuteration (%) Bis-allylic |
|---|---|---|---|---|---|---|---|
| 8 | 4 (1%) | T-Lnn | No | 7 | >99 | 22 | 95 |
| 9 | 4 (5%) | T-Ara | No | 3 | n.i. | 17 | 95 |
| 10[h] | 4 (3%) | E-Lnn E-Ara E-DHA | No | 1 | n.i. | 17 | 96 |
| 11 | 4 (1%) | O-Lnn | No | 18 | n.i. | 21 (26, 16)[g] | 96 |
| 12 | 4 (1%) | H-Lnn | No | 18 | n.i. | 36 (46, 26)[g] | 98 |
| 13 | 4 (2%) | O-DHA | No | 18 | n.i. | 47 (57, 38)[g] | 98 |
| 14 | 4 (2%) | H-DHA | No | 18 | n.i. | 30 (36, 24)[g] | 98 |
| 15 | 5 (1%) | E-Lnn | No | 24 | n.d. | 0 | 0 |
| 16 | 6 (1%) | E-Lnn | No[i] | 24 | n.d. | N/A[e] | N/A[e] |
| 17[j] | 4 (2%) | POLY | No | 24 | n.i. | 90 | N/A |
| 18[k] | 4 (1%) | HEXD | No | 2 | n.i. | 95 | 0 | n.d. = not determined;
n.i. = not isolated.
[a]equiv. of D$_2$O with respect to a bis-allylic position.
[b]% of complex with respect to the substrate.
[c]73 equiv. of D$_2$O used.
[d]regardless of the presence or absence of D$_2$O.
[e]conjugation or cis/trans isomerisation prevented the estimation on the % deuteration.
[f]73 equiv. of D$_2$O and 60° C.
[g]Combination of $^1$H and $^{13}$C NMR spectroscopy allowed for estimation of the deuteration percentage at the aliphatic mono-allylic position on one end and ester/alcohol/reduced-aliphatic mono-allylic position on the other for select substrates.
[h]1:1:1 mol ratio of the substrates.
[i]cis/trans isomerisation observed with no conjugation.
[j]5 equiv. of D$_2$O.
[k]20 equiv. of D$_2$O.

The deuteration of the bis-allylic position of E-Lnn with complex 4 was achieved by adding E-Lnn to an excess of D$_2$O in the acetone solution at 60° C., obtaining ethyl linolenate (E-Lnn) as 94% bis-allylic and 19% of mono-allylic protons underwent H/D exchange (entry 5, Table 1), signifying selective isotopic modification.

Complex 4 was tested in the deuteration reaction and proved to be an efficient catalyst for the site-specific deuteration than the other investigated complexes tested. It is possible that the phosphine ligand in 1, 2 and 3 (including the imidazolyl moiety in 1) were not involved in the deuteration process. Nevertheless, the presence of cyclopentyl ring seems to be quite important as complex 5 (FIG. 4) showed low activity towards E-Lnn (entry 7, Table 1). However, complex 6 (FIG. 4), which is a permethylated analogue of 4, was shown to perform only cis-trans isomerization without any hints at the target deuteration when E-Lnn was used as the substrate.

Ethyl arachidonate (E-Ara, entry 6, Table 1), ethyl docosahexaenoate (E-DHA, entry 7, Table 1), the triglycerides of linolenic (T-Lnn; entry 8, Table 1) and arachidonic (T-Ara; entry 9, Table 1) acids were successfully and selectively deuterated at bis-allylic positions with complex 4. It was also possible to perform the selective H/D exchange using a mixture of E-Lnn, E-Ara and E-DHA (mass ratio of 1:1:1, entry 10, Table 1), signifying a great potential to eliminate costly separations among various PUFAs. The alcohol (O-Lnn and O-DHA; entries 11 and 13) and hydrocarbon (H-Lnn and H-DHA; entries 12 and 14) analogues of E-Lnn and E-DHA were also adequate substrates for the target deuteration. The average deuteration at the bis-allylic position was around 95% while the mono-allylic positions were deuterated at about 25% or less for select substrates. A higher degree of deuteration (about 98%) at the bis-allylic position was possible but with loss of selectivity with respect to the monoallylic positions (see, for example, entries 12 and 13, Table 1). By using $^{13}$C NMR spectroscopy, it was possible to estimate the relative percentage of deuteration at different (aliphatic vs ester/alcohol/reduced-aliphatic) mono-allylic positions. In all cases, the mono-allylic sites with a longer chain or presence of ester/alcohol groups were deuterated to a lesser extent presumably due to a higher steric influence (e.g. entry 7, Table 1).

Controlled experiments were performed by using H$_2$O instead of D$_2$O in order to examine whether any cis-trans isomerisation occurs for the reaction conditions used in Table 1. It has been reported that an allylic position of E-Lin in $^{13}$C NMR spectra was downfield shifted by about 5 ppm for each double bond that had been isomerized from cis to trans. For example, the bis-allylic positions in E-Lnn have two adjacent double bonds and hence if any one of these double bonds is isomerized to trans the 6c signal would be downfield shifted by about 5 ppm. If both bonds are isomerized to trans, then the shift is about 10 ppm. Using this information, experiments described in Table 2 wherein D$_2$O was replaced with H$_2$O were repeated, confirming by $^{13}$C NMR spectroscopy that there was no formation of any trans-containing isomer for any of the PUFAs attempted.

Without wishing to be bound by any theory, it is believed that the experimental data collected thus far indicated that the mechanism of deuteration using complex 4 was different from the one described for other organic substrates. Considering that complex 4 (i) deuterates E-Lin only at the mono-allylic positions, (ii) deuterates bis-allylic positions of the systems with three or more double bonds (E-Lnn, E-Ara, E-DHA) and (iii) causes no cis-trans isomerisation in these PUFAs, it was then likely that the anionic allylic intermediate was not involved in the overall mechanism for the observed H/D exchange. Without wishing to be bound by any theory, it is believed that a possible intermediate for the deuteration of a bis-allylic position of E-Lnn is shown in FIG. 5. Without wishing to be bound by any theory, it is believed that the substrate binds to the ruthenium center through two double bonds, which would bring the protons of one of the bis-allylic sites closer to the metal center, creating a Ru H contact (agositc interaction). This Ru H contact would then increase the acidity of the proton, allowing for the target H/D exchange without any cis-trans isomerization or the formation of a conjugate system. This intermediate would lead to the mono-allylic selectivity for E-Lin, as the sole bis-allylic position of this substrate would be facing away from the ruthenium center. It would also result in the deuteration selectivity of the mono-allylic positions based on the steric demand of the pendant groups, which was the case for E-DHA (entry 9, Table 1).

The direct bis-allylic deuteration method described herein efficiently modified various PUFAs using a number of Ru-based complexes (FIG. 4). Complex (2), compared to Complex 1 gave no double bond conjugation but this complex could only perform the deuteration of the mono-allylic positions of E-Lin. However, using E-Lnn resulted in deuteration of the bis-allylic positions as well. The phosphine ligand in complexes 1, 2 and 3, apart from the reaction rates, had no influence on the target deuterations leading to complex 4 being the most viable option. Lastly, H/D exchange at the bis-allylic position of E-Lnn, E-Ara, E-DHA and T-Lnn, with a minimal deuteration at the mono-allylic positions, were achieved with complex 4.

The H/D exchange using polybutadiene and cis-1,4-hexadiene was also tested. Even though the solubility of cis-polybutadiene was not ideal in the acetone/$D_2O$ mixture, there was evidence to suggest that this polymer could also be deuterated at the mono-allylic positions (POLY; entry 17, Table 1). As this material contains two methylene groups between the alkene fragments it indicated that the described deuteration was not limited to only skipped alkenes (e.g. PUFAs). Furthermore, successful H/D exchange was also performed at the allyl-$CH_3$ group of cis-1,4-hexadiene (HEXD; entry 18, Table 1) emphasizing that the existence of chemically different alkene groups could be used for the deuteration.

The role of the Cp ligand in the Ruthenium catalyst was also studied. Hexa(acetonitrile) complex 5 (FIG. 4) showed no deuteration ability using E-Lnn signifying the importance of the cyclic substituent (entry 15, Table 1). However, if the permethylated analogue was used (i.e. complex 6; FIG. 4), only cis-to-trans isomerisation was observed (entry 16, Table 1). The rates of the cis-trans isomerisation of polyunsaturated alkenes progressively increased with sequential addition of methyl fragments to the Cp ring possibly due to the loosening of one of the Ru-alkene bonding interactions as the Cp ring is methylated.

Without wishing to be bound by any theory, it is believed that Complex 1 formed a conjugated system when E-Lin was used as the substrate, and it might be ineffective for catalyzing the target bis-allylic deuterations. Forming a more sterically demanding complex (2) resulted in the absence of double bond conjugation and selective deuteration of the mono-allylic positions of E-Lin. Without wishing to be bound by any theory, it is believed that the redundancy of the entire imidazolyl-phosphine ligand was supported by the activity of complex 3, and more importantly complex phosphine-free complex 4. Complex 4 was then used to perform selective deuteration of various substrates including polybutadiene and cis-1,4-hexadiene. Without wishing to be bound by any theory, it is believed that the mechanism may involve the formation of a bis-alkene intermediate, which is unlike any other mechanism described for deuteration of various organic substrates.

In most cases (e.g., entries 1~4 and 9-18, Table 1) the reaction was prepared and monitored using a J. Young NMR tube according to the following procedure: A J. Young NMR tube was charged with 10 mg of a substrate followed by $D_2O$ (73 or 100 equiv. per bis-allylic position; or 5 equiv. for polybutadiene per methylene group due to solubility issues) and acetone-$d_6$ (~0.5 ml) after which first $^1H$ NMR spectrum was acquired. Inside a glove box a ruthenium complex was dissolved in acetone-$d_6$ (~0.3 ml) and transferred in the tube and heated if necessary. Reaction progress was monitored by hourly $^1H$ NMR scans during first 12 hours followed by daily scans.

For select runs (entries 5-8, Table 1) the reaction was performed using 100 mg of substrates to emphasize that virtually quantitative yields of these reactions could be obtained: Inside a glove box two scintillation vials were charged with a substrate (E-Lnn, E-Ara, E-DHA or T-Lnn) and complex 4, respectively. Both were transferred into two separate Schlenk flasks using three 0.5 ml acetone portions each. $D_2O$ was added to the flask containing PUFA followed by the amount of acetone necessary to form a homogenous solution. Then a solution of complex 4 in acetone was transferred to the substrate/$D_2O$-containing solution reaction was left stirring at room temperature. Upon completion of the reaction, excess of 2 N HCl (not less than 5 times volume of reaction mixture) was added and the mixture was allowed to stir vigorously for 15 minutes. The product was extracted with 100 ml of hexane and the solution was then washed with saturated $NaHCO_3$ and NaCl solutions and dried over anhydrous $NaSO_4$. The solution was filtered and activated carbon was added. Stirring for another 15 minutes, filtration and removal of volatiles in vacuo afforded desired product.

General Procedure a for Deuteration of E-Lin and E-Lnn with Various Ruthenium Complexes (Table 1)

A J Young NMR tube was charged with PUFA followed by $D_2O$ and acetone-$d_6$, after which first $^1H$ NMR spectrum was acquired. Inside a glove box, PUFA solution was then transferred into a scintillation vial containing respective ruthenium complex. The resulting solution was thoroughly mixed and transferred back into the NMR tube. Reaction progress was monitored by hourly $^1H$ NMR scans during first 12 hours followed by daily scans.

General Procedure B for Deuteration of Various PUFAs Using Complex 4

Inside a glove box two scintillation vials were charged with PUFA and complex 4, respectively. Both were transferred into two separate Schlenk flasks using three 0.5 ml acetone portions each. $D_2O$ was added to the flask containing PUFA followed by the amount of acetone necessary to form a homogenous solution. Then a solution of complex 4 in acetone was added to a solution of PUFA via the cannula and reaction was left stirring at room temperature. Upon completion of the reaction, excess of 2 N HCl (not less than 5 times volume of reaction mixture) was added and the mixture was allowed to stir vigorously for 15 minutes. The product was extracted with 100 ml of hexane and the solution was then washed with saturated $NaHCO_3$ and NaCl solutions and dried over anhydrous NaSO$_4$. The solution was filtered and activated carbon was added. Stirring for another 15 minutes, filtration and removal of volatiles in vacuo afforded desired product.

Synthesis of Deuterated Ethyl Linolenate (E-Lnn)

General procedure B was followed by mixing together 100 mg of E-Lnn (0.326 mmol), 1.18 ml of D2O (65.40 mmol) and 1.42 mg of complex 4 (1%, 3.26 mol) in 10 ml of acetone and stirring for 1 hour to afford desired deuterated product as clear colorless oil (101.06 mg, 99.6% yield).

Synthesis of Deuterated Ethyl Arachidonate (E-Ara)

General procedure B was followed by mixing together 100 mg of E-Ara (0.301 mmol), 1.63 ml of D2O (90.22 mmol) and 1.31 mg of complex 4 (1%, 3.01 mol) in 12.5 ml of acetone and stirring for 24 hours to afford desired deuterated product as clear colourless oil (101.36 mg, 99.5% yield).

Synthesis of Deuterated Ethyl Docosahexaenoate (E-DHA)

General procedure B was followed by mixing together 100 mg of E-DHA (0.280 mmol), 2.53 ml of D2O (0.14 mol) and 2.44 mg of complex 4 (2%, 5.61 μmol) in 15 ml of acetone and stirring for 18 hours to afford desired deuterated product as clear colourless oil (101.96 mg, 99.8% yield).

Synthesis of Deuterated Trilinolenin (T-Lnn)

General procedure B was followed by mixing together 100 mg of T-Lnn (0.115 mmol), 1.24 ml of D$_2$O (68.70 mmol) and 0.50 mg of complex 4 (1%, 1.15 mmol) in 20 ml of acetone and stirring for 7 hours to afford desired deuterated product as clear colourless oil (101.34 mg, 99.7% yield).

CONCLUSION

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A composition comprising a compound having the formula:

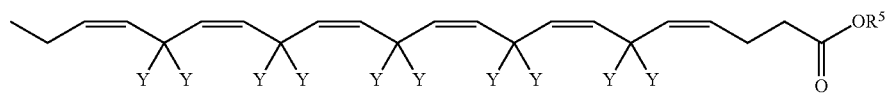

wherein $R^5$ is H, $C_1$-$C_5$ alkyl, or a cation; and each Y is independently H, deuterium, or tritium, and at least one Y is deuterium or tritium, wherein the compound comprises at least 5% of the total number of molecules in the composition.

2. The composition of claim 1, wherein $R^5$ is $C_1$-$C_5$ alkyl.

3. The composition of claim 2, wherein $R^5$ is ethyl.

4. The composition of claim 1, wherein two or more Y is deuterium.

5. The composition of claim 4, wherein the compound has an isotopic load that is in a range from 5% to 30%.

6. The composition compound of claim 4, wherein the isotopic load is in a range from to 10% to 20%.

7. The composition of claim 4, wherein the isotopic load is in a range from 5% to 15%.

8. The composition of claim 1, wherein the compound comprises 5% to 99% of the total number of molecules in the composition.

9. The composition of claim 1, wherein the compound comprises 5% to 50% of the total numbers of molecules in the composition.

10. A composition comprising a compound having the formula:

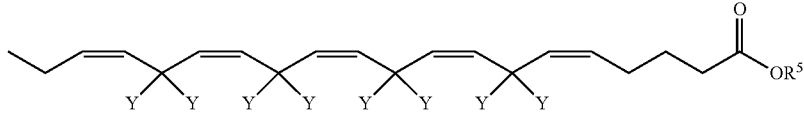

wherein $R^5$ is H, $C_1$-$C_5$ alkyl, or a cation; and each Y is independently H, deuterium, or tritium, and at least one Y is deuterium or tritium, wherein the compound comprises at least 5% of the total number of molecules in the composition.

11. The composition of claim 10, wherein $R^5$ is $C_1$-$C_5$ alkyl.

12. The composition of claim 11, wherein $R^5$ is ethyl.

13. The composition of claim 10, wherein two or more Y is deuterium.

14. The composition of claim 13, wherein the compound has an isotopic load that is in a range from 5% to about 20%.

15. The composition of claim 13, wherein the isotopic load is in a range from about 10% to about 20%.

16. The composition of claim 13, wherein the isotopic load is in a range from about 5% to about 15%.

17. The composition of claim 10, wherein the compound comprises 5% to 99% of the total number of molecules in the composition.

18. The composition of claim 10, wherein the compound comprises 5% to 50% of the total number of molecules in the composition.

19. The composition of claim 1 or 10, wherein the composition does not comprise trans isomers of said compound.

* * * * *